US006994981B2

(12) United States Patent  (10) Patent No.: US 6,994,981 B2
Sperandio et al.  (45) Date of Patent: Feb. 7, 2006

(54) MODULATORS OF PARAPTOSIS AND RELATED METHODS

(75) Inventors: Sabina Sperandio, San Diego, CA (US); Susana Castro-Obregon, Novato, CA (US); Dale E. Bredesen, Novato, CA (US)

(73) Assignee: The Buck Institute, Novato, CA (US)

( * ) Notice: Subject to any disclaimer, the term of this patent is extended or adjusted under 35 U.S.C. 154(b) by 47 days.

(21) Appl. No.: 10/202,503

(22) Filed: Jul. 23, 2002

(65) Prior Publication Data

US 2005/0244894 A1  Nov. 3, 2005

Related U.S. Application Data

(63) Continuation-in-part of application No. 10/079,929, filed on Feb. 19, 2002.

(51) Int. Cl.
  *G01N 33/53* (2006.01)
(52) U.S. Cl. ............................... 435/7.21; 435/6; 435/4
(58) Field of Classification Search ................ 424/9.2; 514/2, 44; 435/7.1, 7.21, 7.2, 6, 4; 436/501
  See application file for complete search history.

(56) References Cited

U.S. PATENT DOCUMENTS 6,063,758 A * 5/2000 Lappi et al. .................... 514/2

FOREIGN PATENT DOCUMENTS

WO  WO 02/064128 A1 *  8/2002

OTHER PUBLICATIONS

Wyllie et al. (2001), More than one way to go, PNAS 98(1): 11-13.*
Kang et al. (2001), Regulation of apoptosis by somatostatin and substance P in peritoneal macrophages, Regul. Pept. 101(1-3): 43-49.*
Arck et al., "Indications for a brain-hair follicle axis: inhibition of keratinocyte proliferation and up-regulation of keratinocyte apoptosis in telogen hair follicles by stress and substance P," *FASEB J.* 15:2536-2538 (2001).
Arck, P., "Stress and Pregnancy Loss: Role of Immune Mediators, Hormones and Neurotransmitters," *Am. J. Reprod. Immunol.* 46:117-123 (2001).
Atkinson et al., "Cytotoxic T Lymphocyte-assisted Suicide. Caspase 3 Activation is Primarily the Result of the Direct Action of Granzyme B," *J. Biol. Chem.* 273:21261-21266 (1998).
Bhatt and Ferrell, "The Protein Kinase p90 Rsk as an Essential Mediator of Cytostatic Factor Activity," *Science* 286:1362-1365 (1999).
Böckmann et al., "Delay of neutrophil apoptosis by the neuropeptide substance P: involvement of caspase cascade," *Peptides* 22:661-670 (2001).
Bohm et al., "Identification of Potential Tyrosine-containing Endocytic Motifs in the Carboxyl-tail and Seventh Transmembrane Domain of the Neurokinin 1 Receptor," *J. Biol. Chem.* 272:2363-2372 (1997).
Bonni et al., "Cell Survival Promoted by the Ras-MAPK Signaling Pathway by Transcription-Dependent and -Independent Mechanisms," *Science* 286:1358-1362 (1999).
Chan et al., "Bradykinin antagonist dimer, CU201, inhibits the growth of human lung cancer cell lines by a "biased agonist" mechanism," *Proc. Natl. Acad. Sci. USA* 99:4608-4613 (2002).
Chang and Karin, "Mammalian MAP kinase signalling cascades," *Nature* 410:37-40 (2001).
Chi et al., "Oncogenic Ras triggers cell suicide through the activation of a caspase-independent cell death program in human cancer cells," *Oncogene* 18:2281-2290 (1999).
Dal Canto and Gurney, "Development of Central Nervous System Pathology in a Murine Transgenic Model of Human Amyotrophic Lateral Sclerosis," *American Journal of Patholology* 145:1271-1279 (1994).
DeFea et al., "The proliferative and antiapoptotic effects of substance P are facilitated by formation of a β-arrestin-dependent scaffolding complex," *Proc. Natl. Acad. Sci. USA* 97:11086-11091 (2000).
del Rio et al., "APAP, a sequence-pattern recognition approach identifies substance P as a potential apoptotic peptide," *FEBS Lett.* 494:213-219 (2001).

(Continued)

*Primary Examiner*—Robert C. Hayes
*Assistant Examiner*—Daniel Gamett
(74) *Attorney, Agent, or Firm*—McDermott Will & Emery LLP

(57) ABSTRACT

The invention is directed to a method of identifying a compound that modulates SP-induced paraptosis by (a) contacting a population of cells with an effective amount of substance P to induce SP-induced paraptosis; (b) contacting a first sub-population of the cells with a test-compound, and a second sub-population of the cells with a control-compound; and (c) comparing the amount of cell death between the first and second sub-populations of cells, where a difference in the amount of cell death between the first and second sub-populations of cells indicates that the test-compound is a compound that modulates SP-induced paraptosis. The invention is also directed to a method of treating a condition associated with excessive cell accumulation by administering to a subject in need of such treatment an effective amount of a compound identified from the method described above where the effective amount of the compound increases SP-induced paraptosis. The invention is further directed to a method of treating a condition associated with excessive cell death by administering to a subject in need of such treatment an effective amount of a compound identified from the method described above where the effective amount of the compound decreases SP-induced paraptosis.

10 Claims, 10 Drawing Sheets

OTHER PUBLICATIONS

Dimri et al., "Specific Inibition of Glucocorticoid-Induced Thymocyte Apoptosis by Substance P," *The Journal of Immunology* 164:2479-2486.

Ellerby et al., "Anti-cancer activity of targeted pro-apoptotic peptides," *Nat. Med.* 5:1032-1038 (1999).

English et al., "New Insights into the Control of Map Kinase Pathways," *Exp. Cell Res.* 253:255-270 (1999).

Fong et al., "Differential Activation of Intracellular Effector by Two Isoforms of Human Neurokinin-1 Receptor," *Mol. Pharmacol.* 41:24-30 (1992).

Graves et al., "Regulation of carbamoyl phosphate synthetase by MAP kinase," *Nature* 403:328-332 (2000).

Hershey and Krause, "Molecular characterization of a functional cDNA encoding the rat substance P receptor," *Science* 247:958-962 (1990).

Hongo et al., "Inhibition of Tumorigenesis and Induction of Apoptosis in Human Tumor Cells by the Stable Expression of a Myristylated COOH Terminus of the Insulin-like Growth Factor I Receptor," *Cancer Research* 58:2477-2484 (1998).

Krause et al., "Three Rat Preprotachykinin mRNAs Encode the Neuropeptides Substance P and Neurokinin A," *Proc. Natl. Acad. Sci. USA* 84:881-885 (1987).

Li et al., "A substance P (neurokinin-1) receptor mutant carboxyl-terminally truncated to resemble a naturally occurring receptor isoform displays enhanced responsiveness and resistance to desensitization," *Proc. Natl. Acad. Sci. USA* 94:9475-9480 (1997).

Liu et al., "Expression of the Insulin-like Growth Factor I Receptor C Terminus as a Myristylated Protein Leads to Induction of Apoptosis in Tumor Cells," *Cancer Research* 58:570-576 (1998).

Liu et al., "Mice Carrying Null Mutations of the Genes Encoding Insulin-like Growth Factor I (Igf-1) and Type 1 IGF Receptor (Igf1r)," *Cell* 75:59-72 (1993).

Liu et al., "Substance P is expressed in hippocamal principal neurons during status epilepticus and plays a critical role in the maintenance of status epilepticus," *Proc. Natl. Acad. Sci. USA* 96:5286-5291 (1999).

Liu et al., "Resistance to excitotoxin-induced seizures and neuronal death in mice lacking the preprotachykinin A gene," *PNAS* 96:12096-12101 (1999).

Majno and Joris, "Apoptosis, Oncosis, and Necrosis; An Overview of Cell Death," *American Journal of Pathology* 146:3-15 (1995).

Murray et al., "Inhibition of the p44/42 MAP kinase pathway protects hippocampal neurons in a cell-culture model of seizure activity," *Neurobiology* 95:11975-11980 (1998).

Plymate et al., "Type-1 Insulin-Like Growth Factor Receptor Reexpression in the Malignant Phenotype of SV40-T-Immortalized Human Prostate Epithelial Cells Enhances Apoptosis," *Endocrine* 7:119-124 (1997).

Quartara and Maggi, "The tachykinin $NK_1$ receptor. Part I: ligands and mechanisms of cellular activation," *Neuropeptides* 31:537-563 (1997).

Rosati et al., "Induction of Apoptosis by a Short-Chain Neuropeptide Analog in Small Cell Lung Cancer," *Peptides* 19:1519-1523 (1998).

Rundén et al., "Regional Selective Neuronal Degeneration after Protein Phosphatase Inhibition in Hippocampal Slice Cultures: Evidence for a MAP Kinase-Dependent Mechanism," *The Journal of Neuroscience* 18:7296-7305 (1998).

Seabrook et al., "L-733,060, a novel tachykinin $NK_2$ receptor antagonist; effects in $[Ca^{2+}]_1$ mobilisation, cardiovascular and dural extravasation assays," *European Journal of Pharmacology* 317:129-135 (1996).

Sperandio et al., "An alternative, nonapoptotic form of programmed cell death," *Proc. Natl. Acad. Sci. USA* 97:14376-14381 (2000).

Stennicke et al., "Pro-caspase-3 Is a Major Physiologic Target of Caspase-8," *J. Biol. Chem.* 273:27084-27090 (1998).

Tennant et al., "Protein and Messenger Ribonucleic Acid (mRNA) for the Type 1 Insulin-Like Growth Factor (IGF) Receptor Is Decreased and IGF-II mRNA Is Increased in Human Prostate Carcinoma Compared to Benign Prostate Epithelium," *J. Clin. Endocrinol. Metab.* 81:3774-3782 (1996).

Treinies et al., "Activated MEK Stimulates Expression of AP-1 Components Independently of Phosphatidylinositol 3-Kinase (PI3-Kinase) but Requires a PI3-Kinase Signal to Stimulate DNA Synthesis," *Mol. Cell. Biol.* 19:321-329 (1999).

Turmaine et al., "Nonapoptotic neurodegeneration in a transgenic mouse model of Huntington's disease," *Proc. Natl. Acad. Sci. USA* 97:8093-8097 (2000).

Vink et al., "An Overview of New and Novel Pharmacotherapies for Use in Traumatic Brain Injury," *Clin. Exp. Pharmacol. Physiol.* 28:919-921 (2001).

Vito et al., "Cloning of AIP1, a Novel Protein That Associates with the Apoptosis-linked Gene ALG-2 in a $Ca^{2+}$-dependent Reaction," *The Journal of Biological Chemistry* 274:1533-1540 (1999).

Wellington et al., "Inhibiting Caspase Cleavage of Huntingtin Reduces Toxicity and Aggregate Formation in Neuronal and Nonneuronal Cells," *The Journal of Biological Chemistry* 275:19831-19838 (2000).

Xia et al., "Opposing effects of ERK and JNK-p38 MAP kinases on apoptosis. (extracellular signal-regulated kinase; c-JUN NH2-terminal protein kinase; mitogen-activated protein kinase)," *Science* 270:1326-1331 (1995).

Yu et al., "Neurokinin-1 receptor antagonist SR140333: a novel type of drug to treat cerebral ischemia," *Neuroreport* 8:2117-2119 (1997).

Zachrisson et al., "A tachykinin $NK_1$ receptor antagonist,, CP-122, 721-1, attenuates kainic acid-induced seizure activity," *Molecular Brain Research* 60:291-295 (1998).

* cited by examiner

Death or Death Decision

Figure 2

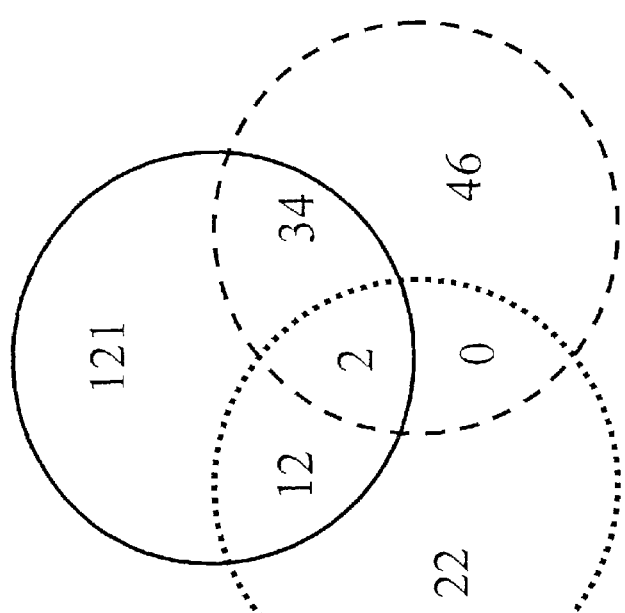

1.7 fold or greater differential expression
50% or greater spot area
200 or greater probe signal strength
Induced and repressed genes combined Numbers in circles indicate the number of differentially expressed genes identified using a 7075 gene Human unigene cDNA gene expression microarray. Numbers in the outer portions of tehcircles are the uniquely expressed genes, those in the intersections are common to both experiments. Note the lack of overlap (only 2 of 116 transcripts) between paraptosis and apoptosis.

Figure 3

Apoptosis vs. Paraptosis: Inhibitors

| | Apoptosis | Paraptosis |
|---|---|---|
| p35 | Inhibits | No |
| xiap | Inhibits | No |
| zVAD.fmk | Inhibits | No |
| BAF | Inhibits | No |
| Bcl-xL | Inhibits | No |
| Bcl-2 | Inhibits | No |

Figure 4

Apoptosis vs. Paraptosis: Morphology

|  | Apoptosis | Paraptosis |
|---|---|---|
| Nuclear fragmentation | Yes | No |
| Chromatin condensation | Yes | Slight |
| Cytoplasmic vacuolation | No | Yes |
| Mitochondrial swelling | Some | Some |
| Blebbing | Yes | No |
| Apoptotic bodies | Yes | No |

Figure 5

Apoptosis vs. Paraptosis: Biochemistry

|  | Apoptosis | Paraptosis |
|---|---|---|
| DEVD-cleaving activity | Yes | No |
| Caspase-3 processing | Yes | No |
| TUNEL staining | Yes | No |
| Internucleo-somal DNA cleavage | Yes | No |

Figure 6A
Figure 6B
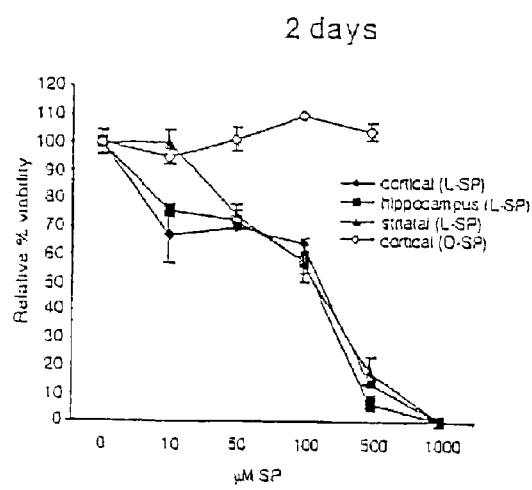
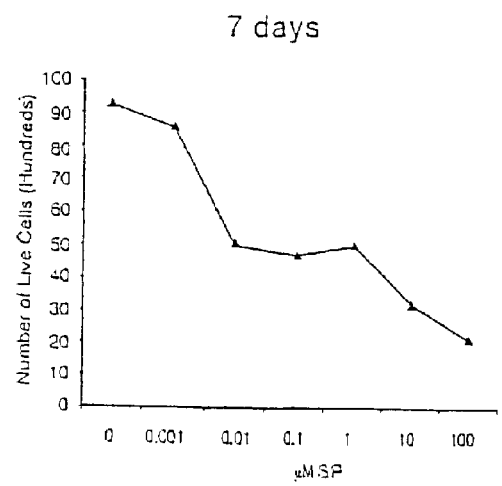

ial cell deaths, such as autophagic cell death and cytoplasmic cell death, do not resemble apoptosis. Furthermore, neurodegenerative diseases such as Huntington's disease and amyotrophic lateral sclerosis are characterized by neuronal cell death that is nonapoptotic. In addition, ischemia-induced cell deaths may also display a non-apoptotic morphology, referred to as "oncosis." The biochemical mechanisms involved in these alternative forms of cell death remain largely unknown. However, discovery of their existence means that modulation of the apoptotic pathway genetically or pharmacologically may prove ineffective in situations in which such nonapoptotic cell death occurs.

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct

<400> SEQUENCE: 1

Asp Glu Val Asp
 1

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
ggtctattgc cccaaaatgg ataacg                                    26

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
ctgaattcaa gatggctaga ggcatgcc                                  28

<210> SEQ ID NO 4
<211> LENGTH: 39
<212> TYPE: DNA
<213> ORGANISM: Artificial Sequence
<220> FEATURE:
<223> OTHER INFORMATION: Primer

<400> SEQUENCE: 4
gtggacctgg ccttcgctca ggcctgcatg gctgcattc                      39

<210> SEQ ID NO 5
<211> LENGTH: 45
<212> TYPE: DNA
<213> ORGANISM: Artificial Sequence
<220> FEATURE:
<223> OTHER INFORMATION: Primer
```

-continued

```
<400> SEQUENCE: 5
ggaaatgaaa tccacccgat acctctaggc atattcaagg catgc            45
```

MODULATORS OF PARAPTOSIS AND RELATED METHODS

This application is a continuation-in-part of U.S. application Ser. No. 10/079,929, filed Feb. 19, 2002, which is incorporated herein by reference in its entirety.

This invention was made with government support under grant number AG12282 awarded by the National Institutes of Health. The United States Government has certain rights in this invention.

BACKGROUND OF THE INVENTION

The present invention relates generally to molecular medicine and programmed cell death and more specifically to methods of modulating non-apoptotic programmed cell death. Apoptosis is the most common and best understood of the programs of cell death. The central set of cysteine-aspartyl proteases or caspases that drive the process are instrumental in the vast majority of apoptotic events that occur during normal embryonic development, as was initially illustrated in studies of the nematode *Caenorhabditis elegans* where elimination of the caspase homologue led to complete cessation of the 131 programmatic cell deaths that normally occur during development of that organism. The role of caspase-driven apoptotic events in human pathogenesis is less clear. However, recent evidence supports the theory that caspase cleavage of mutant proteins may represent an important signaling event in the initiation of cell death in a variety of degenerative conditions.

Despite the widespread occurrence of apoptosis in physiological and pathological cell death, the occurrence of cell deaths that fulfill criteria for neither apoptosis nor necrosis has been well documented. For example, certain developmental cell deaths, such as autophagic cell death and cytoplasmic cell death, do not resemble apoptosis. Furthermore, neurodegenerative diseases such as Huntington's disease and amyotrophic lateral sclerosis are characterized by neuronal cell death that is nonapoptotic. In addition, ischemia-induced cell deaths may also display a non-apoptotic morphology, referred to as "oncosis." The biochemical mechanisms involved in these alternative forms of cell death remain largely unknown. However, discovery of their existence means that modulation of the apoptotic pathway genetically or pharmacologically may prove ineffective in situations in which such nonapoptotic cell death occurs.

One form of programmed cell death that is distinct from apoptosis by the criteria of morphology, biochemistry and response to apoptosis inhibitors has been termed "paraptosis." Despite its lack of response to caspase inhibitors and Bcl-$X_L$, paraptotic cell death has been shown to be induced, among other inducers, by insulin-like growth factor I receptor (IGFIR) and mediated by an alternative caspase-9 activity that is Apaf-1 independent. In addition, as disclosed herein, substance P (SP) can induce a form of paraptotic cell death.

Nonapoptotic cell death has been implicated in developmental cell death, neurodegenerative diseases and cancer. Thus, a need exists to identify compounds that modulate paraptosis or SP-induced paraptosis and develop methods for both the induction and inhibition of paraptosis or SP-induced paraptosis. The present invention satisfies this need and provides related advantages as well.

SUMMARY OF THE INVENTION

The invention is directed to a method of inducing paraptotic cell death in a cell by contacting the cell with an effective amount of a compound selected from the group consisting of ceramide, Tumor Necrosis Factor (TNF), caspase-7, caspase-8, α-amino-3-hydroxy-5-methyl-4-isoxazole proprionic acid (AMPA), kainic acid and glutamic acid, wherein the effective amount of the compound induces paraptotic death of the cell. The invention further is directed to a method of inhibiting paraptotic cell death in a cell by contacting the cell with an effective amount of a compound selected from the group consisting of Alg-2-interacting protein 1 (AIP-1), Jun N-terminal kinase 1 (JNK1) neutralizing agent, Jun N-terminal kinase 2 (JNK2) neutralizing agent, TNF Receptor-Associated Factor 2 (TRAF2) neutralizing agent, ortho-phenanthroline and the JNK inhibitor SP 600125, wherein the effective amount of the compound inhibits paraptotic death of the cell.

Also provided by the invention is a method of treating a condition associated with excessive cell accumulation by administering to a subject in need of such treatment an effective amount of a compound selected from the group consisting of ceramide, Tumor Necrosis Factor (TNF), caspase-7, caspase-8, α-amino-3-hydroxy-5-methyl-4-isoxazole proprionic acid (AMPA), kainic acid and glutamic acid, wherein the effective amount of the compound induces paraptotic cell death. The invention further provides a method of treating a condition associated with excessive cell death by administering to a subject in need of such treatment an effective amount of a compound selected from the group consisting of Alg-2-interacting protein 1 (AIP-1), Jun N-terminal kinase 1 (JNK1) neutralizing agent, Jun N-terminal kinase 2 (JNK2) neutralizing agent, TNF Receptor-Associated Factor 2 (TRAF2) neutralizing agent, ortho-phenanthroline and the JNK inhibitor SP 600125, wherein the effective amount of the compound inhibits paraptotic cell death.

The invention further provides a method of identifying a compound that modulates substance P (SP)-induced paraptosis by (a) contacting a population of cells with an effective amount of substance P to induce SP-induced paraptosis; (b) contacting a first sub-population of the cells with a test-compound, and a second sub-population of the cells with a control-compound; and (c) comparing the amount of cell death between the first and second sub-populations of cells, where a difference in the amount of cell death between the first and second sub-populations of cells indicates that the test-compound is a compound that modulates SP-induced paraptosis.

The invention also provides a method of treating a condition associated with excessive cell accumulation by administering to a subject in need of such treatment an effective amount of a compound that modulates SP-induced paraptosis where the effective amount of the compound increases SP-induced paraptosis. The invention further provides a method of treating a condition associated with excessive cell death by administering to a subject in need of such treatment an effective amount of a compound that modulates SP-induced paraptosis where the effective amount of the compound decreases SP-induced paraptosis.

BRIEF DESCRIPTION OF THE DRAWINGS

FIG. 2 shows a diagram demonstrating differential gene expression in paraptosis and apoptosis, with co-epression of only 2 of 116 transcripts.

FIG. 3 shows a table setting forth the lack of effect on paraptotic cell death of various apoptosis inhibitors.

FIG. 4 shows a table setting forth morphological differences observed between apoptosis and paraptosis.

FIG. 5 shows a table setting forth biochemical distinctions observed between apoptosis and paraptosis.

FIG. 6A shows the relative percentage of cell viability for neurons treated with the L or D isomer of SP. FIG. 6B shows the number of live striatal cells after growth in the indicated concentrations of SP.

DETAILED DESCRIPTION OF THE INVENTION

The invention is directed to methods of modulating paraptosis with compounds that have the ability either to induce or to inhibit this particular form of programmed cell death. Paraptosis, a form of programmed cell death, is implicated in conditions involving cell death-inducing insults as well as in conditions associated with the inhibition of cell death. Therefore, compounds that modulate paraptosis, can be used therapeutically in the treatment of a variety of conditions including neoplastic conditions, autoimmune conditions, neurodegenerative conditions and ischemic conditions.

The methods of the invention for modulating paraptosis have therapeutic value for a variety of conditions associated with aberrant levels of paraptosis. For example, the invention methods can be used to treat those types of neurodegeneration associated with nonapoptotic cell death such as, for example, familial amyotrophic lateral sclerosis as described by Dal Canto and Gurney, *American Journal of Pathology* 145:1271–1279 (1994); Huntington's Disease as described by Turmaine et al., *Proc. Natl. Acad. Sci. USA* 97:8093–8097 (2000). Notably, there is no evidence that the majority of neural cell death in other neurodegenerative diseases including Parkinson's Disease and Alzheimer's Disease is apoptotic in nature.

Figure 1:
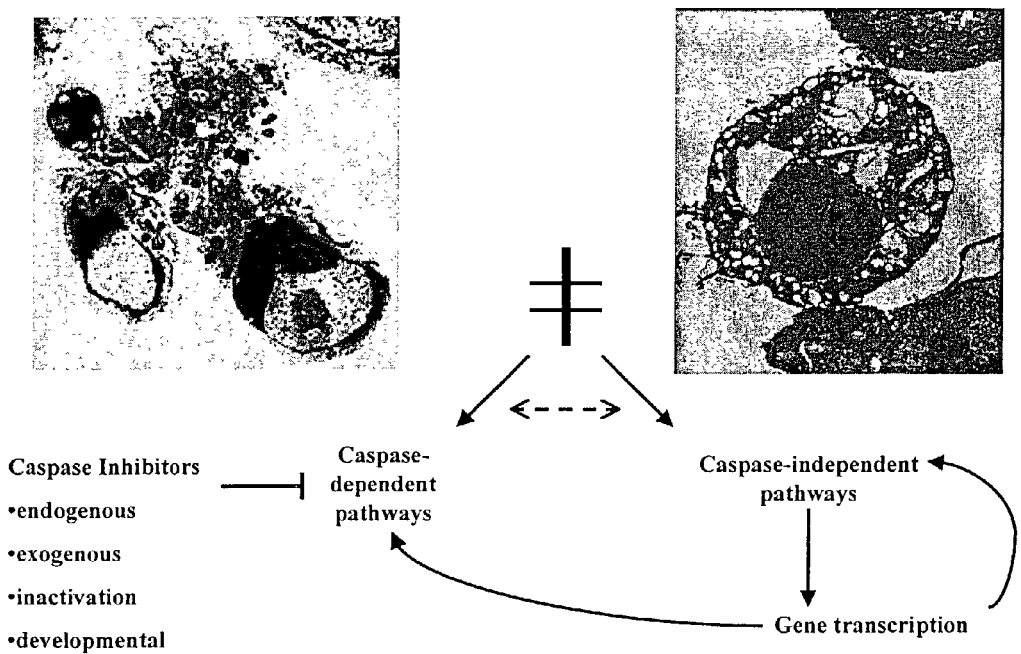
FIG. 1 shows a schematic that demonstrates that paraptosis and apoptosis together represent a two-pronged response to death-inducing insults.

As shown in FIG. 1, cell-death inducing insults can lead to a two-pronged response, where one arm of the pathway is caspase-dependent and leads to apoptotic cell death, while a separate arm that is caspase independent leads to paraptotic cell death. Receptors involved in mediating cell death may activate either the paraptotic or apoptotic pathway, or may activate both pathways. Receptors that activate the paraptotic pathway, for example, Insulin-Like Growth Factor I Receptor (IGFIR), typically inhibit caspases. Receptors that can activate both pathways, for example, the TNF-α receptor, typically respond to caspase inhibition by switching from activation of the apoptotic pathway to activation of the paraptotic pathway.

Whether cell death occurs via paraptosis or apoptosis depends on a variety of factors, including, for example, the cell type and the type of insult. In particular, if a cell is contacted with a toxin such as, for example, a sulfhydryl oxidizing agent such as diethylmaleate, and damage to the endogenous caspases results in their inactivation, then cell death will occur via the paraptotic pathway. Similarly, if the cell that is subjected to the insult is producing an endogenous caspase inhibitor, for example, xiap, apoptosis also is blocked in favor of paraptosis. Gene expression from the non-caspase cell death pathway leads to upregulation of both pro-paraptotic and pro-apoptotic molecules. As described herein, inhibitors or neutralizing agents of the Jun N-terminal kinases (JNKs) JNK1 and JNK2, which are MAP kinases activated in response to cellular stress, block both the paraptotic and the apoptotic cell death pathways. Furthermore as described herein, Tumor Necrosis Factor (TNF) and ceramide are two compounds that can induce paraptosis.

Cross-talk between the paraptotic and apoptotic pathways is a further feature of programmed cell death. For example, caspase-9 can induce the paraptotic pathway in an Apaf-1-independent manner as described in Sperandio et al., *Proc. Natl. Acad. Sci. USA* 97:14376–14381 (2000), which is incorporated herein by reference. In addition and as described herein, caspase-7 and caspase-8 also can induce the paraptotic pathway, but unlike for caspase-9, induction by these two caspases is subject to inhibition by, for example, zVAD.fmk, BAF amd p35. In addition, caspase-7 inhibitors include, for example, xiap and Ac-DEVD, and caspase-8 inhibitors include, for example, IETD.fmk and crmA.

Insulin-Like Growth Factor I Receptor (IGFIR), as well as the IGFIR intracytoplasmic domain (IGFIR-IC), are paraptosis-mediating molecules that induce a form of non-apoptotic programmed cell death characterized by cytoplasmic vacuolation and resistance to apoptosis inhibitors. This form of cell death, designated paraptosis, requires transcription and de novo protein synthesis. In addition, a microarray screening comparing gene expression profiles between IGFIR induced cell death and apoptotic cell death showed that fewer than 2% of those genes that are differentially expressed are shared between the two cell death programs, a finding consistent with distinct cell death programs. As shown in FIG. 2, a Human unigene microarray of 7075 genes shows an overlap of only 2 of 116 transcripts between paraptosis and apoptosis.

Paraptotic cell death has been implicated in a variety of pathological and normal cellular events. Overexpression of fragments of the intracellular domain of IGFIR in cancer cells has been shown to reduce tumorigenicity in nude mice and induce cell death (see, Hongo et al., *Cancer Research* 58:2477–2484 (1998); Liu et al., *Cancer Research* 58:570–576 (1998)). The expression of IGFIR is decreased in prostate cancer (Tennant et al., *J. Clin. Endocrinol. Metab.* 81:3774–82 (1996) 1, and its reexpression in immortalized human prostate cells inhibited the malignant phenotype (Plymate et al., *Endocrine* 7:119–24 (1997)). Moreover, a potential role for IGFIR in developmental cell death is suggested by the phenotype of IGFIR-null mice, which includes a higher neuronal density in the brain stem and spinal cord (Liu et al. *Cell* 75:59–72 (1993)). The paraptotic form of programmed cell death induced by IGFIR and IGFIR-IC has been shown to be distinct from apoptosis based on morphological, biochemical and molecular features as described in Sperandio et al., supra, 2000, which is incorporated herein by reference in its entirety.

Paraptosis is a nonapoptotic form of programmed cell death that can be induced by IGFIR and is mediated by a newly identified function of caspase-9 that is distinct from the role of caspase-9 in the apoptotic pathway as described in Sperandio et al., supra, 2000. Thus, caspase-9 participates in both, apoptotic and paraptotic forms of cell death. However, as shown in FIG. 3, caspase inhibitors that inhibit apoptosis fail to inhibit paraptosis, an indication that distinct catalytic activities of caspase-9 mediate apoptosis and paraptosis. IGFIR co-imminoprecipitates with caspase-9 and mutants of IGFIR that fail to coimmunoprecipitate with caspase-9 also fail to induce paraptosis. The pro-apoptotic and the pro-paraptotic effects of caspase-9 can be distinguished by the lack of effect of caspase inhibitors including, for example, BAF, zVAD.fmk, p35, and xiap on paraptosis; lack of a requirement of paraptosis for activation of caspase-9 zymogen by Apaf-1; and lack of suppression of paraptosis by mutation catalytic sites of caspase-9 as described in Sperandio et al., supra, 2000. Thus, caspase-9 has at least two distinct activities, one that is pro-apoptotic and one that induces paraptotic cell death.

The invention is also directed to the discovery of a ligand-receptor pair that induces a form of paraptosis. As described herein, substance P (SP) and its receptor, neurokinin-1 receptor (NK1R), a ligand-receptor pair that is widely distributed in the central and peripheral nervous systems, can induce a form of paraptosis. This ligand-receptor pair has previously been implicated in pain mediation and depression, among other effects.

SP fits a biophysical profile for pro-apoptotic peptides and SP can induce cytochrome c release in a cell-free system of apoptosis (Ellerby, Nat Med 5:1032–1038 (1999), del Rio et al., FEBS Lett. 494:213–219 (2001)). However, extracellular SP is not toxic to fibroblasts even at millimolar concentrations, indicating that the pro-apoptotic effect of SP requires internalization. As disclosed herein, and in contrast to the effect of SP on fibroblasts, nanomolar concentrations of SP are neurotoxic in primary cultures of striatal, cortical, and hippocampal neurons, and induce a delayed cell death. All three types of neurons are sensitive to micromolar concentrations of SP after 48 hours of exposure to SP (FIG. 6A) and to nanomolar concentrations of SP after seven days of exposure (FIG. 6B). However, the dying cells do not show apoptotic bodies or other characteristic features of apoptosis, and instead the cells are vacuolated.

SP is an eleven amino acid containing neurotransmitter belonging to the tachykinin family of peptides, members of which display some similarity in amino acid sequence in their carboxy-termini. SP is an alternatively spliced product of the preprotachykinin A gene (PPTA) that binds with nanomolar affinity to the neurokinin-1 receptor (NK1R). NK1R is a G-protein coupled receptor connected by various second messengers to a wide variety of effector mechanisms to modulate cellular function. Three apparently independent second messenger systems can be activated by G-proteins following ligand binding to NK1R: 1) $Ca^{++}$ mobilization from both intra- and extracellular sources via stimulation of phospholipase C; 2) arachidonic acid mobilization via phospholipase A2; and 3) cAMP accumulation via stimulation of adenylate cyclase (Quartara and Maggi, Neuropeptides 31:537–563 (1997)). An alternative pathway, through interaction with β- arrestin, involves the activation of the MAPK pathway, leading to ERK1 and 2 ERK2 activation (DeFea et al., Proc. Natl. Acad. Sci. USA 97:11086–11091 (2000)).

The development of specific agonists and antagonists for NK1R has supported a role for NK1R in numerous biological processes, such as pain transmission in the spinal cord. In the CNS, NK1R also regulates cardiovascular and respiratory function, and is involved in activating the emetic reflex. NK1R also regulates several behavioral responses, and has recently been implicated in depression and schizophrenia. NK1R can be involved in a wide variety of functions due to its ability to modulate the release of other neurotransmitters, such as excitatory amino acids (Quartara and Maggi, supra, 1998).

SP also plays an important role in pathological states in which neural cell death occurs, such as status epilepticus and ischemia. For example, SP null mice demonstrate resistance to excitotoxin-induced seizures, with an associated reduction in neuronal death (Liu et al., Proc. Natl. Acad. Sci. USA 96:12096–12101 (1999)). Similarly, treatment with an antagonist for NK1R inhibits seizures and reduces kainic acid-induced cell death in the CA1 region of the hippocampus. Furthermore, in a model of focal cerebral ischemia, administration of an NK1R antagonist reduced infarct volume and improved neurological function (Yu et al., Neuroreport 8:2117–2119 (1997)). Recent evidence has shown that SP antagonists can decrease lesion volume and improve neurologic outcome in traumatic brain injury (Vink et al., Clin. Exp. Pharmacol. Physiol. 28:919–921 (2001). Outside the nervous system SP also mediates processes where cell death occurs, such as stress-induced hair loss and stress-triggered abortion (Arck et al., FASEB J. 15:2536–2538 (2001); Arck, P. C., Am. J. Reprod. Immunol. 46:117–123 (2001)).

As disclosed herein, SP induces a form of programmed cell death in primary cultures of hippocampal, cortical and striatal neurons that is caspase-independent and requires new gene expression to occur. Morphologically, this form of cell death does not resemble apoptosis, since there is no membrane blebbing, nuclear fragmentation or phosphatidylserine translocation. As further disclosed herein, expression of NK1R in non-neuronal cells converts these cells into SP-sensitive cells, reproducing the cell death morphology observed in primary neurons. Ultrastructurally, cells undergoing SP-induced non-apoptotic cell death exhibit vacuolation and show some phagolysosomes, while the plasma and nuclear membranes remain intact. Unlike apoptosis, SP-induced non-apoptotic cell death is not prevented by caspase inhibitors, nor by over-expression of Bcl-xL. Due to the similarities between the disclosed SP-induced non-apoptotic cell death and paraptosis, we have labeled SP-induced non-apoptotic cell death as "SP-induced paraptosis."

SP-induced paraptosis can be blocked in cells that contain a mutant form of NK1R that fails to activate the MAPK pathway but retains the ability to interact with G-proteins. The role of the MAPK pathway in SP-induced paraptosis is further evidenced by the discovery that pharmacological inhibition of a MAPKK prevents this form of cell death. Therefore, the invention provides a ligand-receptor pair and associated signal transduction system useful for the identification and modulation of paraptosis and SP-induced paraptosis.

In one embodiment, the invention provides a method of inducing paraptotic cell death in a cell by contacting the cell with an effective amount of a compound selected from the group consisting of ceramide, Tumor Necrosis Factor (TNF), caspase-7, caspase-8, α-amino-3-hydroxy-5-methyl-4-isoxazole proprionic acid (AMPA), kainic acid and glutamic acid, where the effective amount of the compound induces paraptotic cell death.

In a further embodiment, the invention provides a method of inhibiting paraptotic cell death in a cell by contacting the cell with an effective amount of a compound selected from the group consisting of Alg-2-interacting protein 1 (AIP-1), Jun N-terminal kinase 1 (JNK1) neutralizing agent, Jun N-terminal kinase 2 (JNK2) neutralizing agent, TNF Receptor-Associated Factor 2 (TRAF2) neutralizing agent, orthophenanthroline and the JNK inhibitor SP 600125, wherein the effective amount of the compound inhibits paraptotic death of the cell.

In another embodiment, the invention provides a method of identifying a compound that modulates SP-induced paraptosis by (a) contacting a population of cells with an effective amount of substance P to induce SP-induced paraptosis; (b) contacting a first sub-population of the cells with a test-compound, and a second sub-population of the cells with a control-compound; and (c) comparing the amount of cell death between the first and second sub-populations of cells, where a difference in the amount of cell death between the first and second sub-populations of cells indicates that the test-compound is a compound that modulates SP-induced paraptosis.

As used herein, the term "paraptotic cell death" or "paraptosis" refers to programmed non-apoptotic cell death that can be mediated by caspase-9 and lacks many of the molecular, biochemical and cytological characteristics of apoptosis. Paraptosis and apoptosis represent two separate programs of cell death that are induced via distinct molecular pathways, but may be induced simultaneously by a single insult or agent. One feature distinguishing paraptotic cell death from apoptotic cell death is that paraptotic cell death is not affected by caspase inhibitors. In particular, inhibition of apoptosis by the caspase inhibitors zVAD.fmk, BAF, p35m, X-chromosome-linked inhibitor of apoptosis (xiap), Bcl-2, and Bcl-2 family member Bcl-xL are features associated with apoptosis that are not observed or greatly reduced in non-apoptotic cell death. A further distinction between paraptotic cell death and apoptotic cell death is the dependence of apoptotic cell death on Apaf-1, the cytosolic cofactor of caspase-9 zymogen. The mediation of paraptotic cell death when caspase-9 is a mediator is a function of caspase-9 that is distinct from the role of caspase-9 in the apoptotic pathway as evidenced, for example, by the Apaf-1 independence of the paraptotic pathway.

With regard to morphological distinctions between paraptotic and apoptotic cell death, nuclear fragmentation, apoptotic body formation and chromatin condensation are ultrastrucural features of apoptosis that are not observed or are greatly reduced in paraptosis. Furthermore, paraptosis can be associated with cytoplasmic vacuolation, a feature not observed in apoptosis. In addition to being distinct from apoptotic cell death, paraptosis is further distinct from non-programmed cell death, known as necrosis. For example, cleavage of poly(ADP-ribose)polymerase (PARP) yielding distinctive 50 to 62 kDa fragments is a feature of necrosis that is not observed in nonapoptic cell death. Thus, paraptotic cell death is a non-apoptotic form of programmed cell death.

As used herein, the term "SP-induced paraptosis" refers to a form of paraptosis that is induced by substance P (SP). SP-induced paraptosis shares the same or similar morphological features as described above for paraptosis. In particular, paraptosis and SP-induced paraptosis both result in cytoplasmic vacuolation, but do not result in nuclear fragmentation, apoptotic body formation and chromatin condensation, which are features associated with apoptosis. Also, inhibition of cell death by the caspase inhibitors zVAD.fmk and BAF are features associated with apoptosis that are not observed or are greatly reduced in paraptosis and SP-induced paraptosis. In addition to being distinct from apoptotic cell death, SP-induced paraptosis is also distinct from necrosis. For example, SP-induced paraptosis is sensitive to actinomycin D and cycloheximide whereas this sensitivity is not observed with necrosis.

Paraptosis induced by IGFIR and paraptosis induced by SP show many similarities including, for example, similar morphological and caspase inhibitor profiles. In addition, both paraptosis induced by IGFIR and paraptosis induced by SP can be inhibited by Alg-2-interacting protein 1 (AIP-1). Furthermore, both paraptosis induced by IGFIR and paraptosis induced by SP can be inhibited by UO126, which a broad inhibitor of MEK 1 and MEK 2. However, there are some differences between paraptosis induced by IGFIR compared to paraptosis induced by SP. For example, SP-induced paraptosis can be blocked by PD 98059, a known inhibitor of MEK 1, whereas IGFIR-induced paraptosis is not blocked by PD 98059. Another difference between SP-induced paraptosis and IGFIR-induced paraptosis is that IGFIR-induced paraptosis can be blocked by dominant negative caspase 9 expression while SP-induced paraptosis is not blocked by dominant negative caspase 9, but is blocked by dominant negative caspase 3 expression.

SP-induced paraptosis can occur in cells within the nervous system, such as neurons in the central or peripheral nervous system, and in cells outside the nervous system provided that the cells outside of the nervous system can activate the appropriate signaling pathway. For example, non-neuronal cells that express the neurokinin-1 receptor (NK1R) can undergo paraptosis.

As used herein, the term "substance P" or "SP" refers to a polypeptide with substantially the same amino acid sequence as that shown for substance P in Genbank Accession No. NM_012666 that can induce SP-induced paraptosis. "Substantially the same amino acid sequence" is intended to mean an amino acid sequence contains a considerable degree of sequence identity or similarity, such as at least 70%, 80%, 90%, 95%, 98%, or 100% sequence identity or similarity, to a reference amino acid sequence. Conservative and non-conservative amino acid changes, gaps, and insertions to an amino acid sequence can be compared to a reference sequence using available algorithms and programs such as the Smith-Waterman algorithm and the BLAST homology search program (Altschul et al., *J. Mol. Biol.* 215: 403–410 (1990)).

It is understood that fragments of SP which retain substantially the same ability to induce SP-induced paraptosis as the entire polypeptide are included within the definition. Fragments can include, for example, amino terminal, carboxyl terminal, or internal deletions of a full length SP polypeptide. For example, a fragment can contain at least about 4, 6, 8, or 9 or more contiguous or non-contiguous amino acid residues of a full-length SP polypeptide. Polypeptide fragments can be generated, for example, using recombinant DNA methods or enzymatic or chemical cleavage of larger polypeptides. In addition, various molecules, such as other polypeptides, carbohydrates, or lipids, or small molecules can be attached to SP including fragments of SP. For example, a label moiety such as a radioisotope or fluorophore can be attached to SP.

It is understood that limited modifications to the SP polypeptide can be made without destroying the ability of SP to induce SP-induced paraptosis. For example, SP is intended to include other SP family members such as those polypeptides that are found to exhibit the above sequence homologies. Such members include, for example, homologs of SP that can be cloned from other organisms such as humans, monkeys, cows, mice, chickens, frogs, flies, or worms. Sequences of homologs of rat SP are available, for example, in the GenBank database.

Various modifications of the SP primary amino acid sequence can result in polypeptides having substantially equivalent, decreased, or enhanced function as compared to the sequence set forth in Genbank Accession No. NM_012666 (Krause et al., *Proc. Natl. Acad. Sci. USA* 84:881–885 (1987)). Those skilled in the art recognize that such modifications can be desirable at times in order to enhance the bioactivity, bioavailability, or stability of SP, or to facilitate its synthesis or purification. Contemplated amino acid substitutions to the native sequence of SP can include, for example, conservative changes, wherein a substituted amino acid has similar structural or chemical properties such as, for example, replacement of a polar amino acid with another polar amino acid or replacement of a charged amino acid with a similarly charged amino acid. A modification can also be a non-conservative change, for example, replacement of an uncharged polar amino acid with a non-polar amino acid or replacement of a charged amino acid with an uncharged polar amino acid, where the substituted amino acid has different but sufficiently similar structure or chemical properties so as to not affect adversely the described biological function of SP. In addition, a variety of polypeptide modifications are known in the art for constraining the structure of polypeptides to enhance stability or binding, for example, the generation of a cyclic peptide (Cabezas and Satterthwait, *J. Am. Chem. Soc.* 121: 3862–3875 (1999); Stanfield et al., *Structure* 7:131–142 (1999)).

A polypeptide can be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like. Chemical modifications of the polypeptide such as, for example, alkylation, acylation, carbamylation, and iodination can also be used so long as the polypeptide retains its ability to induce SP-induced paraptosis.

Those skilled in the art can determine which residues and which regions of a SP sequence are likely to be tolerant of modification and still retain an ability to induce SP-induced paraptosis. For example, amino acid substitutions or chemical or enzymatic modifications at residues that are less well conserved between species are more likely to be tolerated than substitutions at highly conserved residues. Accordingly, an alignment can be performed among SP sequences of various species to determine residues and regions in which modifications are likely to be tolerated. Additional guidance for determining residues and regions of SP likely to be tolerant of modification is provided by studies of SP fragments and variants. For example, a carboxy-terminal fragment of SP (SP 6–11) is known to retain good affinity for the NK1 receptor. In addition, several variants of SP have been characterized (Quartara, *Neuropeptides* 31: 537–563 (1997)).

As used herein, the term "neurokinin-1 receptor" or "NK1R" refers to a polypeptide with substantially the same amino acid sequence as that shown in Genbank Accession No. M31477 that can specifically bind to SP. The term "specifically binds" is intended to mean the polypeptide will have an affinity for the target polypeptide that is measurably higher than its affinity for a non-specific interaction. NK1R can bind to SP with low or high affinity so long as the binding is sufficient to be detectable. For example, NK1R can bind SP with a binding affinity (Kd) of about $10^{-4}$ M or less, $10^{-5}$ M or less, $10^{-6}$ M or less, about $10^{-7}$ M or less, including about $10^{-8}$ M or less, such as $10^{-9}$ M or less. Several methods for detecting or measuring polypeptide binding are known in the art.

It is understood that a fragment of NK1R can be sufficient in order to produce this activity. For example, fragments of NK1R which retain substantially the same ability to specifically bind to SP as the entire polypeptide are included within the definition. Fragments can include, for example, amino terminal, carboxyl terminal, or internal deletions of a full length SP polypeptide. For example, a fragment can contain at least about 50, 100, 150, 200, 250, 300, 350, 400, or more contiguous or non-contiguous amino acid residues of a full-length NK1R polypeptide. Polypeptide fragments can be generated, for example, using recombinant DNA methods or enzymatic or chemical cleavage of larger polypeptides. In addition, various molecules, such as other polypeptides, carbohydrates, or lipids, or small molecules can be attached to NK1R including fragments of NK1R. For example, a label moiety such as a radioisotope or fluorophore can be attached to NK1R.

It is understood that limited modifications to the NK1R polypeptide can be made without destroying the ability of NK1R to specifically bind to SP. For example, NK1R is intended to include other NK1R family members such as those polypeptides that are found to exhibit the above sequence homologies. Such members include for example, homologs of NK1R that can be cloned from other organisms such as humans, monkeys, cows, mice, chickens, guinea pigs, frogs, flies, and worms. Sequences of homologs of rat NK1R are available, for example, in the GenBank database. For example, the GenBank accession number for a mouse NK1R is NM_009313.1.

Various modifications of the NK1R primary amino acid sequence can result in polypeptides having substantially equivalent, decreased, or enhanced function as compared to the sequence set forth in Genbank Accession No. M31477 (Hershey and Krause, *Science* 247:958–962 (1990)). Those skilled in the art recognize that such modifications can be desirable at times in order to enhance the bioactivity, bioavailability or stability of NK1R, or to facilitate its synthesis or purification. Contemplated amino acid substitutions to the native sequence of NK1R can include, for example, conservative changes, wherein a substituted amino acid has similar structural or chemical properties such as, for example, replacement of a polar amino acid with another polar amino acid or replacement of a charged amino acid with a similarly charged amino acid. A modification can also be a non-conservative change, for example, replacement of an uncharged polar amino acid with a non-polar amino acid or replacement of a charged amino acid with an uncharged polar amino acid, where the substituted amino acid has different but sufficiently similar structure or chemical properties so as to not affect adversely the described biological function of NK1R. In addition, a variety of polypeptide modifications are known in the art for constraining the structure of polypeptides to enhance stability or binding (Cabezas and Satterthwait, supra, 1999; Stanfield et al., supra, 1999).

A polypeptide can be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like. Chemical modifications of the polypeptide such as, for example, alkylation, acylation, carbamylation, and iodination can also be used so long as the polypeptide retains its ability to specifically bind to SP.

Those skilled in the art can determine which residues and which regions of a NK1R sequence are likely to be tolerant of modification and still retain an ability to specifically bind to SP. For example, amino acid substitutions or chemical or enzymatic modifications at residues that are less well conserved between species are more likely to be tolerated than substitutions at highly conserved residues. Accordingly, an alignment can be performed among NK1R sequences of various species to determine residues and regions in which modifications are likely to be tolerated. Additional guidance for determining residues and regions of NK1R likely to be tolerant of modification is provided by studies of NK1R fragments and variants. For example, a naturally occurring isoform of human NK1R containing 311 amino acids (compared to 407 amino acids in full length NK1R) has been isolated which binds SP with 10-fold lower affinity than the full length form of NK1R (Fong, *Mol. Pharmacol.* 41:24–30 (1992)).

As used herein, the phrase "in a cell" is intended to mean within a living organism or living cell. A living organism includes for example, multi-cellular organisms such as a human, animal, insect, or worm, and uni-cellular organisms such as a single-celled protozoan, yeast cell, or bacterium. In addition, a living cell derived from an organism used directly or grown in cell culture is an in vivo environment that also is encompassed by the phrase "in a cell." For example, an oocyte removed from an organism such as a frog used directly or grown in a tissue culture dish would constitute an in vivo environment encompassed by the phrase "in a cell."

As used herein, the term "neutralizing agent" is intended to refer to an agent effecting a decrease in the activity, amount or rate of expression of the reference molecule or compound, for example, Jun N-terminal kinase 1 (JNK1) or JNK2.

Neutralizing agents useful for practicing the claimed invention include, for example, binding molecules such as antibodies as well as molecules that modulate or regulate the activity, amount or rate of expression of the reference molecule or compound through non-binding interactions. A neutralizing agent can be, for example, any molecule that binds JNK1, JNK2, TRAF2, ERK2, or any other reference molecule with sufficient affinity to decrease its activity. Additionally, a neutralizing agent can be any molecule binds to a regulatory molecule or gene region so as to inhibit or promote the function of the regulatory protein or gene region and effect a decrease in the extent or amount or rate of expression or activity of JNK1, JNK2, TRAF2, ERK2, or any other reference molecule. Thus, a neutralizing agent can be any molecule that directly or indirectly modulates or regulates the extent, amount or rate of expression or activity of JNK1, JNK2, TRAF2, ERK2, or any other reference molecule. For example, a peptide or peptidomimetic that binds JNK1, JNK2, TRAF2, ERK2, or any other reference molecule with sufficient affinity to decrease activity, respectively, is useful for practicing the claimed methods. In addition, examples of neutralizing agents which effect a decrease in the expression of JNK1, JNK2, TRAF2, ERK2, or any other reference molecule can include antisense nucleic acids and transcriptional inhibitors.

As used herein, the term "effective amount" is intended to mean an amount that produces a desired effect. For example, when used in reference to a compound that induces SP-induced paraptosis, it is intended to mean an amount of the compound sufficient to induce SP-induced paraptosis. In addition, when used in reference to a compound or molecule that modulates a form of paraptotic cell death, it is intended to mean an amount of the compound or molecule sufficient to modulate a form of paraptotic cell death or to treat or reduce the severity of a condition in an affected subject.

The term "paraptosis-modulating compound" refers to a compound that has the ability to increase (or induce), decrease (or inhibit) or otherwise modify the rate or amount of any form of paraptosis. As used herein, the term "compound that modulates SP-induced paraptosis" refers to a compound that has the ability to increase (or induce), decrease (or inhibit) or otherwise modify the rate or amount of SP-induced paraptosis. The term "paraptosis-modulating compound" as used herein is a general term that includes a "compound that modulates SP-induced paraptosis." A paraptosis-modulating compound can act by altering directly or indirectly the severity, extent, intensity, magnitude, duration or frequency of paraptotic cell death. A paraptosis-modulating compound can also, for example, alter the severity, extent, intensity, magnitude, duration or frequency of a symptom associated with paraptosis or SP-induced paraptosis. A paraptosis-modulating compound can modulate SP-induced paraptosis by altering the expression of an endogenous paraptosis-mediating molecule such as, for example, SP, NK1R, or a MAPK signaling pathway protein. An "endogenous paraptosis-mediating molecule," as used herein, is a molecule that plays a role in the molecular pathway that regulates paraptosis or SP-induced paraptosis in vivo. The role of an endogenous paraptosis-mediating molecule can be that of a positive or a negative regulator. Examples of endogenous paraptosis-mediating molecules that mediate SP-induced paraptosis include, for example, SP or NK1R and the like.

As used herein, the term "compound" is intended to mean an isolated macromolecule of natural or synthetic origin that can be assayed using the methods of the invention. A compound includes, for example, a polypeptide, including an antibody, glycoprotein or lipoprotein, a peptidomimetic, a non-peptidyl compound, a nucleic acid including an aptamer, a carbohydrate, a lipid, or a small organic or inorganic molecule. For example, a compound can be an isolated cDNA sequence. A compound can have a known or unknown structure. A compound can be isolated or be part of a population of compounds such as a library. For example, a compound can be a small organic compound obtained from a combinatorial chemical library. A library of compounds can be a random collection of compounds or can be rationally designed based on a physical characteristic.

As used herein, the term "control compound" is intended to mean a compound that is used in a method of the invention that serves as a control for the compound that is being tested, referred to herein as the "test-compound." As understood by those of skill in the art, methods for identifying compounds that modulate an activity generally require comparison to a control. One type of control is a reaction or cell that is treated substantially the same as the reaction or cell exposed to the test-compound, with the distinction that the control reaction or cell is not exposed to the test-compound. Instead, a control compound can be used which is inactive in the assay. For example, a control compound can be a buffer or vehicle that was used in the preparation of the test compound. Also, for example, a control compound can have a similar structure to a test-compound but no activity in the assay. In addition, a control reaction can be performed by adding no compound.

As used herein, the term "population" is intended to refer to a group of two or more individual molecules or cells. A population can be as large as the number of individual molecules or cells currently available to the user or able to be made by one skilled in the art. Typically, populations can be as small as 2 molecules or cells. In some embodiments, populations can be, for example, hundreds or thousands of molecules or cells, or greater than 105, 106, 107, and 108, molecules or cells. In other embodiments, populations are between about $10^8$–$10^{13}$ or more molecules or cells. Those skilled in the art will know what size of a population is suitable for a particular application.

As used herein, the term "subpopulation" refers to a subgroup of one or more molecules or cells from an original population. The subpopulation can be obtained by, for example, dividing the population into one or more fractions. The subpopulation need not contain equivalent numbers of molecules or cells although roughly equivalent amounts of cells are often used when comparing two or more subpopulations of cells directly.

The invention provides a method of identifying a compound that modulates SP-induced paraptosis by inducing SP-induced paraptosis in a cell, contacting the cell with a test-compound, and identifying a compound that modulates SP-induced paraptosis. For example, in one embodiment, the invention provides a method of screening for a compound that decreases SP-induced paraptosis by inducing SP-induced paraptosis in a cell, contacting the cell with a test-compound and measuring the amount of cell death in the cell, where survival of the cell indicates that the compound decreases SP-induced paraptosis. This type of screening assay is also referred to as a survival screen.

In a related embodiment, the invention provides a method of identifying a compound that modulates SP-induced paraptosis by (a) contacting a population of cells with an effective amount of substance P to induce SP-induced paraptosis; (b) contacting a first sub-population of the cells with a test-compound, and a second sub-population of the cells with a control-compound; and (c) comparing the amount of cell death between the first and second sub-populations of cells, where a difference in the amount of cell death between the first and second sub-populations of cells indicates that the test-compound is a compound that modulates SP-induced paraptosis.

Paraptosis and SP-induced paraptosis can be induced in a variety of ways. Any compound or process that results in cell death that fits the criteria described herein for paraptosis or SP-induced paraptosis can be used in the methods of the invention. A compound useful for practicing the invention method for modulating paraptosis, a term used herein to refer collectively to the processes of inducing (increasing) and inhibiting (decreasing) paraptosis, can act through a variety of mechanisms. For example, a compound can act by altering the association of IGFIR and caspase-9, or SP and NK1-R, in a population of cells and, therefore, can be useful as medicaments for treating a pathology characterized by an aberrant level of paraptosis or SP-induced paraptosis. Such a compound can, for example, decrease the affinity of association of IGFIR and caspase-9 or SP and NK1R.

Paraptosis can be induced, for example, by upregulating caspase-9 in the presence of an apoptosis inhibitor. In this regard, the expression of caspase-9 in the presence of the apoptosis inhibitor BAF (or zVAD.fmk) induces paraptosis as described in Sperandio et al., supra, 2000. Thus, paraptosis can be induced by upregulating caspase-9 in the presence of an apoptosis inhibitor. Similarly, upregulation of caspase-2, caspase-7 or caspase-8, will induce both paraptosis and apoptosis. As shown herein, paraptosis also can be induced by, for example, ceramide, Tumor Necrosis Factor (TNF), caspase-7, caspase-8, α-amino-3-hydroxy-5-methyl-4-isoxazole proprionic acid (AMPA), kainic acid and glutamic acid. In addition, paraptosis can be induced by an environmental stimulus that represents a cell death-inducing insult such as, for example, heat shock, and the like.

SP-induced paraptosis can be induced, for example, by SP, NK1R, or components of the MAPK pathway or by compounds that mimic SP, NK1R, or certain components of the MAPK pathway. Induction of paraptosis by SP can occur through activation of NK1R or through other mechanisms. Likewise, activation of NK1R can occur through the binding of SP or a different compound. For example, a truncated form of SP, SP 6–11, which contains amino acids 6 through 11 of the SP polypeptide, can induce SP-induced paraptosis. In addition, activation of the MAPK pathway can occur through NK1R or through a different mechanism that leads to SP-induced paraptosis.

The carboxy-terminal region of NK1R is known to interact with β-arrestin and, upon SP stimulation, a protein complex is formed that activates the MAPK pathway leading to the activation of ERK-1 and ERK-2. Mammals express at least four distinctly regulated groups of MAPKs, extracellular signal-related kinases (ERK)1/2, Jun amino-terminal kinases (JNK1/2/3), p38 proteins (p38α/γ/γ/δ) and ERK5, that are activated by specific MAPKKs: MEK1/2 for ERK1/2, MKK3/6 for the p38s, MKK4/7 for the JNKs, and MEK5 for ERK5. Each MAPKK can in turn be activated by a MAPKK kinase or MEK kinase (MAPKKK or MEKK) (English, J. et al., *Exp. Cell Res.* 253:255–270 (1999); Chang and Karin, *Nature* 410:37–40 (2001)). MAPKs connect cell-surface receptors to regulatory targets, such as transcription factors like the Ets family of transcription factors.

MAPKs are known to regulate cell proliferation and cell survival. For example, ERK1/2 stimulates DNA synthesis through phosphorylation of carbamoyl phosphate synthetase II, a rate-limiting enzyme in pyrimidine nucleotide biosynthesis (Graves et al., *Nature* 403:328–332 (2000)). ERKs are also involved in the inactivation of MYT1 and induction of cyclin D1 through enhancing AP-1 activity (Treinies et al., *Mol. Cell. Biol.* 19:321–329 (1999); Bhatt et al., *Science* 286:1362–1365 (1999)). Generally, activation of ERK1/2 has been linked to cell survival, whereas JNK and p38 are linked to induction of apoptosis (Xia et al., *Science* 270: 1326–1331 (1995)). In cerebellar granular cells, ERK activation by survival factors prevents apoptosis through RSK, which inactivates the pro-apoptotic protein BAD (Bonni et al., *Science* 286:1358–1362 (1999)). ERK may also induce growth factors that promote cell survival.

Paraptosis induced by IGFIR and paraptosis induced by SP show many similarities including, for example, similar morphological profiles. In addition, both paraptosis induced by IGFIR and paraptosis induced by SP can be inhibited by Alg-2-interacting protein 1 (AIP-1) and UO126, which a broad inhibitor of MEK 1 and MEK 2. However, there are some differences between paraptosis induced by IGFIR compared to paraptosis induced by SP. For example, SP-induced paraptosis can be blocked by PD 98059 whereas IGFIR-induced paraptosis is not blocked by PD 98059. Because PD 98059 is a known inhibitor of MEK 1, these results indicate that SP-induced paraptosis can be mediated by the MEK 1 part of the MAP kinase pathway while IGF1R-induced paraptosis can be mediated by the MEK 2 part of the MAP kinase pathway.

Any cell that can be induced to undergo paraptosis or SP-induced paraptosis can be used in the methods of the invention. These cells can be derived from any species so long as the cell can undergo a form of paraptotic cell death. In the case of SP-induced paraptosis, both neuronal or non-neuronal cells can be used. For example, both striatal neurons and human embryonic kidney 293T cells transfected with NK1R can be used in the methods of the invention.

Cells used in the methods of the invention can include primary cells as well as cell lines. Primary cells in a tissue section or grown in cell culture can be used in the invention. For example, primary striatal, cortical, or hippocampal neurons from a mammal can be used in the methods of the invention (see Example III). These neurons can be grown in cell culture either in an isolated form or with other cells that can be used to provide better growth of the neurons. In addition, these neurons can be used in the invention as a tissue slice, for example, a hippocampal tissue slice that is used directly after isolation or that has been maintained in tissue culture. Cell and tissue culture techniques are well known in the art.

Cell lines can also be used in the methods of the invention. Several neuronal and non-neuronal cell lines have been established and are well known in the art. Many of these cell lines are available from the American Type Culture Collection (ATCC) or from individual investigators. Neuronal cell lines that can be used in the invention include, but are not limited to, SH-SY5Y, B103, SK-N-MC, and Neuro2A. In addition, non-neuronal cell lines can be used in the invention. In regard to SP-induced paraptosis, any cell lines that expresses NK1R, or that can be transfected with NK1R, can be used in the invention. For example, non-neuronal cancerous cells and epithelial cells can endogenously express NK1R and undergo AP-induced paraptosis. Non-neuronal cell lines that can be transfected include, for example, 293T, HeLa, COS-7, and Jurkat cells, among others. Transfection techniques, such as calcium phosphate, lipids, and electroporation are well known in the art. Furthermore, stem cells or other pluripotent cells can be used in the invention. These cells can be used either as primary cells or cell lines in either an undifferentiated or differentiated state.

A level of cell death or cell viability can be measured by any of a variety of methods known to one skilled in the art. For example, trypan blue staining can be used to measure the level of cell death in a cell. Other staining methods, for example, propidium iodide and Alomar Blue, also can be used to measure cell death. The stained cells can be visualized in any way that is convenient, for example, by microscopy or flow cytometry (FACS). In addition, cell viability and cell proliferation assays such as the lactose dehydrogenase (LDH) assay and the MTT (3-(4,5-dimethylthiazolyl-2)-2,5-diphenyltetrazolium bromide) assay are commercially available and can be used to measure cell viability. In addition, the uptake of 3H thymidine can be used to access the viability of cells.

Various assays can be used to determine the type of cell death occurring in a cell depending on the experiment. For example, if SP is added to two sub-populations of cells, a standard trypan blue assay and microscopic evaluation of cells can be performed if the object is to determine the level of SP-induced paraptosis in the two sub-populations. In addition, microscopic evaluation of cells allows morphological characterization of dying cells. Also, since several types of cell death can be occurring simultaneously in one population of cells, compounds can be used to block one type of cell death in order to measure the contribution of that type of cell death to the overall level of cell death observed in the cells. For example, caspase inhibitors can be added to cells in order to block apoptotic cell death, but these inhibitors will not block paraptosis or SP-induced paraptosis that can be occurring in the same population of cells.

The invention provides methods of identifying paraptosis or SP-induced paraptosis in a cell by measuring cell death in the presence of dominant negative caspase-9 or a MAPKK inhibitor such as PD 98059. For example, the invention provides a method of identifying paraptosis or SP-induced paraptosis in a cell by measuring the level of caspase-3 activation in the cell, and measuring the level of ERK1 or ERK2 phosphorylation in the cell, where the absence of caspase-3 activation and the presence of ERK1 or ERK2 phosphorylation indicates SP-induced paraptosis in the cell.

Once paraptosis or SP-induced paraptosis has been induced in a cellular system, a compound capable of modulating these processes such as, for example, the compounds administered in the methods of the present invention, can be identified by contacting the cellular system with a test-compound to verify that paraptosis or SP-induced paraptosis is modulated. One skilled in the art will appreciate that further compounds having the same or similar modulating activities as the compounds administered in the invention methods can be identified from among a diverse population of molecules. Methods for producing libraries containing diverse populations of molecules, including chemical or biological molecules such as simple or complex organic molecules, peptides, proteins, peptidomimetics, glycoproteins, lipoproteins, polynucleotides, and the like, are well known in the art (Huse, U.S. Pat. No. 5,264,563, issued Nov. 23, 1993; Blondelle et al., *Trends Anal. Chem.* 14:83–92 (1995); York et al., *Science* 274:1520–1522 (1996); Gold et al., *Proc. Natl. Acad. Sci., USA* 94:59–64 (1997); Gold, U.S. Pat. No. 5,270,163, issued Dec. 14, 1993). Such libraries also can be obtained from commercial sources.

Since libraries of diverse molecules can contain as many as $10^{14}$ to $10^{15}$ different molecules, a screening assay provides a simple means for identifying further compounds that can modulate paraptosis or SP-induced paraptosis. In particular, a screening assay can be automated, which allows for high throughput screening of randomly or rationally designed libraries of compounds to identify further compounds that can modulate paraptosis or SP-induced paraptosis.

A screening assay can be used to identify a compound that modulates paraptosis or SP-induced paraptosis. As used herein, the term screening assay is intended to mean assaying two or more compounds simultaneously in order to identify a compound or compounds with the desired activity. Several formats are available for screening which can allow for a low number or high number of compounds to be screened simultaneously. For example, 10, 100, 1000, 10,000, 100,000, 1,000,000 or more compounds can be assayed simultaneously using low or high through-put formats. Screening assays often utilize isolated cells or tissues but can also use a cell free system such as a chemical or biological solution or a cell free extract derived from cells. In addition, a screening assay can utilize whole organisms or animals. The particular design of a screening assay depends on the particular activity of the compound desired and the available reagents.

Modulation of paraptosis or SP-induced paraptosis using the methods of the invention can be a therapeutic strategy for treatment of a variety of neurodegenerative conditions, ischemic conditions, autoimmune conditions as well as neoplastic conditions as set forth herein. As such, administration of a compound that inhibits paraptosis or SP-induced paraptosis can lead to a reduction in the severity of an ischemic condition, neurodegenerative condition or any other condition that is associated with increased cell death. Neural cell death diseases include neurodegenerative diseases such as retinal degeneration, Huntingtons Disease, Parkinson's Disease and Alzheimer's Disease as well as other diseases associated with the loss of neural cells including, for example, stroke, trauma, global ischemia, hypoxia, seizure-induced excitotoxicity. Exemplary compounds contemplated for inhibiting paraptosis or SP-induced paraptosis include paraptosis-modulating compounds administered in the invention methods and, for example, Alg-2-interacting protein 1 (AIP-1), MEK 1 and MEK 2 inhibitors, ERK2 inhibitors, Jun N-terminal kinase 1 (JNK1) neutralizing agent, Jun N-terminal kinase 2 (JNK2) neutralizing agent, TNF Receptor-Associated Factor 2 (TRAF2) neutralizing agent, ortho-phenanthroline and the JNK inhibitor SP 600125.

Administration of a paraptosis-modulating compound that induces paraptosis or SP-induced paraptosis such as, for example, ceramide, Tumor Necrosis Factor (TNF), caspase-7, caspase-8, α-amino-3-hydroxy-5-methyl- 4-isoxazole proprionic acid (AMPA), kainic acid and glutamic acid, can lead to a reduction in the severity of a neoplastic condition or autoimmune condition or any other condition associated with excessive cell accumulation. In addition, administration of a paraptosis-modulating compound that induces paraptosis such as, for example, SP or a compound that mimics SP can lead to a reduction in the severity of a neoplastic condition, autoimmune condition, or other condition associated with excessive cell accumulation. A "neoplastic condition," as used herein, refers to a condition associated with hyperproliferation of cells and includes benign and malignant expanding lesions of proliferating cells. A neoplastic condition is thus characterized by a reduction or deceleration in cell death resulting from a loss of homeostatic control of the appropriate number of cells in a normal tissue. A benign neoplasm grows in an expansile manner, displacing or compressing surrounding tissues rather than invading them. A malignant neoplasm or cancer, refers to a large group of diseases characterized by uncontrolled growth and spread of abnormal cells and includes any condition of tumors having the properties of anaplasia, invasion, and metastasis.

A paraptosis-modulating compound, which includes a compound that modulates SP-induced paraptosis, can be a compound or molecule that binds IGFIR, SP, NK1R, or another paraptosis-mediating molecule with sufficient affinity to modulate paraptosis or SP-induced paraptosis. One skilled in the art will appreciate that in addition to the compounds taught herein to be modulators of paraptosis or SP-induced paraptosis additional paraptosis-modulating compounds can be identified and can be, for example, a macromolecule, such as polypeptide, nucleic acid, carbohydrate or lipid. Thus, a paraptosis-modulating compound can be an antibody, antisense nucleic acid, small interfering nucleic acid such as a small interfering RNA (siRNA), and any compound identified by the methods herein and known to those skilled in the art. A paraptosis-modulating compound can also be a derivative, analogue or mimetic compound as well as a small organic compound as long as paraptosis or SP-induced paraptosis is modulated in the presence of the compound. The size of a paraptosis-modulating compound is not important so long as the molecule exhibits or can be made to exhibit paraptosis-modulating activity. For example, a paraptosis-modulating compound can be as little as between about one and six, and as large as tens or hundreds of monomer building blocks which constitute a macromolecule or chemical binding molecule. Similarly, an organic compound can be a simple or complex structure so long as it has sufficient paraptosis-modulating activity.

Paraptosis-modulating compounds useful for practicing the methods of the invention include the paraptosis-inducing compounds ceramide, Tumor Necrosis Factor (TNF), caspase-7, caspase-8, α-amino-3-hydroxy-5-methyl-4-isoxazole proprionic acid (AMPA), kainic acid and glutamic acid; and further include the paraptosis-inhibiting compounds Alg-2-interacting protein 1 (AIP-1), Jun N-terminal kinase 1 (JNK1) neutralizing agent, Jun N-terminal kinase 2 (JNK2) neutralizing agent, TNF Receptor-Associated Factor 2 (TRAF2) neutralizing agent, ortho-phenanthroline and the JNK inhibitor SP 600125. In addition to the specific paraptosis-modulating compounds taught herein, paraptosis-modulating compounds also can include, for example, antibodies and other receptor or ligand binding polypeptides of the immune system. Such other molecules of the immune system include for example, T cell receptors (TCR) including CD4 cell receptors. Additionally, cell surface receptors such as integrins, growth factor receptors and chemokine receptors, as well as any other receptors or fragments thereof that bind to an endogenous paraptosis-mediating molecule such as, for example, IGFIR or caspase-9, or can be made to bind to an endogenous paraptosis-mediating molecule, with sufficient affinity to modulate activity are also paraptosis-modulating compounds useful for practicing the methods of the invention. Examples of selective inhibitors of paraptosis include, for example, Alg-2-interacting protein 1 (AIP-1), Jun N-terminal kinase 1 (JNK1) neutralizing agent, Jun N-terminal kinase 2 (JNK2) neutralizing agent, TNF Receptor-Associated Factor 2 (TRAF2) neutralizing agent, ortho-phenanthroline, the JNK inhibitor SP 600125, IGFIR neutralizing agents and transcriptional inhibitors that bind to the IGFIR promoter/regulatory region. Additionally, receptors, ligands, growth factors, cytokines or chemokines, for example, which inhibit the expression of an endogenous paraptosis-mediating molecule are also paraptosis-modulating compounds useful for practicing the methods of the invention. Furthermore, DNA binding polypeptides such as transcription factors and DNA replication factors are likewise included within the definition of the term binding molecule so long as they have selective paraptosis-modulating activity. Finally, polypeptides, nucleic acids and chemical compounds such as those selected from random and combinational libraries can also be paraptosis-modulating compounds.

Paraptosis-modulating compounds can act at any point in the paraptosis or SP-induced paraptosis pathway. For example, a paraptosis-modulating compound can bind to and modulate an endogenous paraptosis-mediating molecule such as, for example, SP, NK1R, or a protein in the MAPK pathway. For example, a paraptosis-modulating compound can modulate the MAP kinase kinase (MAPKK) that phosphorylates ERK1 or ERK2. In addition, a paraptosis-modulating compound can modulate the interaction of proteins involved in a paraptosis or SP-induced paraptosis pathway. For example, a paraptosis-modulating compound can block the interaction between SP and NK1R, or can block the interaction of proteins in a MAPK pathway. Conversely, a paraptosis-modulating compound can increase or stabilize the interaction between SP and NK1R, or can up-regulate the MAPK pathway. Paraptosis-modulating compounds include, for example, small interfering nucleic acids such as a small interfering RNA (siRNA) and antisense nucleic acids that can regulate the expression of genes in a paraptotic pathway, antibodies that can bind to proteins in a paraptotic pathway, or organic molecules that can modulate protein interactions in a paraptotic pathway.

As described above, a paraptosis-modulating compound can be small interfering nucleic acids such as a siRNA. For example, a suitable double-stranded RNA (dsRNA) for RNA interference can contain sense and antisense strands of about 21 contiguous nucleotides corresponding to the gene to be targeted that form 19 RNA base pairs, leaving overhangs of two nucleotides at each 3' end (Elbashir et al., supra; Bass, *Nature* 411:428–429 (2001); Zamore, *Nat. Struct. Biol.* 8:746–750 (2001)). dsRNAs of about 25–30 nucleotides have also been used successfully for RNA interference (Karabinos et al., *Proc. Natl. Acad. Sci.* 98:7863–7868 (2001). dsRNA can be synthesized in vitro and introduced into a cell by methods known in the art. By using RNA interference methods, the targeted RNA is degraded, and translation of the target polypeptide is decreased or abolished.

Paraptosis-modulating compounds can include, for example, antibodies and other receptor or ligand binding polypeptides of the immune system. Such other molecules of the immune system include for example, T cell receptors (TCR) including CD4 cell receptors. Additionally, cell surface receptors such as integrins, growth factor receptors, neuropeptide receptors, and chemokine receptors, as well as any other receptors or fragments thereof that bind to an endogenous paraptosis-mediating molecule such as, for example, SP or NK1R, or can be made to bind to an endogenous paraptosis-mediating molecule, with sufficient affinity to modulate activity are also paraptosis-modulating compounds useful for practicing the methods of the invention. An example of an inhibitor of paraptosis or SP-induced paraptosis can include, for example, a NK1R antisense nucleic acid and transcriptional inhibitors that bind to the NK1R promoter/regulatory region. Additionally, receptors, ligands, growth factors, cytokines or chemokines, for example, which inhibit the expression of an endogenous paraptosis-mediating molecule are also paraptosis-modulating compounds useful for practicing the methods of the invention. Furthermore, DNA binding polypeptides such as transcription factors and DNA replication factors are likewise included within the definition of the term binding molecule so long as they have selective paraptosis-modulating activity. Finally, polypeptides, nucleic acids and chemical compounds such as those selected from random and combinational libraries can also be paraptosis-modulating compounds.

Various approaches can be used for identifying further paraptosis-modulating compounds useful for practicing the invention methods. For example, a paraptosis-modulating compound that inhibits paraptosis or SP-induced paraptosis can be an antibody and other receptor of the immune repertoire that acts as a neutralizing agent for, for example, Jun N-terminal kinase 1 (JNK1), Jun N-terminal kinase 2 (JNK2), TNF Receptor-Associated Factor 2 (TRAF2). Therefore, generating a diverse population of binding molecules from an immune repertoire, for example, can be useful for identifying further paraptosis-modulating compounds in addition to those taught and exemplified herein.

A paraptosis-modulating compound can be identified from a population of selected molecules or from a random population of molecules. Molecules can be selected based on several criteria, for example, structural or functional similarity to an endogenous paraptosis-mediating molecule such as, for example, SP, NK1R or a MAPK signaling pathway molecule. For example, rationally designed libraries of compounds based on the three dimensional structure of SP or ERK1 or ERK2 can be used in the methods of the invention.

Another approach is to use the information available regarding the structure and function of, for example, SP, NK1R, and MAPK pathway members to generate binding molecule populations. For example, a paraptosis-modulating compound can be an antibody and other receptor of the immune repertoire. An antibody that recognizes the catalytic site associated with paraptosis or SP-induced paraptosis is useful for practicing the invention method of inhibiting these processes by preventing association of SP and an endogenous paraptosis-mediating molecule. The normal function of such immune receptors is to bind essentially an infinite number of different antigens and ligands. Therefore, generating a diverse population of binding molecules from an immune repertoire, for example, can be useful for identifying a paraptosis-modulating compound.

A further paraptosis-modulating compound useful for practicing the invention methods can also be identified from a large population of unknown molecules by methods well known in the art. Such a population can be a random library of peptides or small molecule compounds. The population can be generated to contain a sufficient diversity of sequence or structure so as to contain a molecule which will bind to an endogenous paraptosis-mediating molecule such as, for example, SP, NK1R, MAPK signaling pathway proteins, IGFIR, caspase-7, caspase-8 or caspase-9, or their respective nucleic acids. Those skilled in the art will know what size and diversity is necessary or sufficient for the intended purpose. A population of sufficient size and complexity can be generated so as to have a high probability of containing a paraptosis-modulating compound that binds an endogenous paraptosis-mediating molecule such as, for example, SP, NK1R, IGFIR, caspase-7, caspase-8 or caspase-9, with sufficient affinity to modulate activity. Numerous other types of library molecule populations exist and are described further below.

Any molecule that binds to an endogenous paraptosis-mediating molecule, to a gene region that controls expression of such a molecule, or to a regulatory molecule that modulates activity or expression of an endogenous paraptosis-mediating molecule, as well as to any regulatory molecule that modulates IGFIR expression is a paraptosis-modulating compound useful for practicing the invention. For example, a paraptosis-modulating compound can be a regulatory molecule affects an expression of an endogenous paraptosis-mediating molecule such as, for example, SP, NK1R, MAPK signaling pathway proteins, IGFIR, caspase-9, caspase-7, or caspase-8, by modulating the action of a transcription factor that controls or upregulates transcription of the endogenous paraptosis-mediating molecule. In addition, a regulatory molecule that binds with sufficient affinity to a molecule involved in the activation of an endogenous paraptosis-mediating molecule to reduce paraptosis or SP-induced paraptosis is a paraptosis-modulating compound useful for practicing the methods of the invention.

A paraptosis-modulating compound can modulate paraptotic activity by binding to an endogenous paraptosis-mediating molecule, to a regulatory molecule that modulates the activity or expression of an endogenous paraptosis-mediating molecule, or to a gene region that controls expression of an endogenous paraptosis-mediating molecule. For example, a paraptosis-modulating compound useful for practicing the claimed invention can be an antibody against a regulator molecule that modulates expression or activity of an endogenous paraptosis-mediating molecule.

A moderate sized population for identification of a further paraptosis-modulating compound useful for practicing the methods of the invention can consist of hundreds and thousands of different binding molecules within the population, whereas a large sized binding molecule population will consist of tens of thousands and millions of different binding molecule species. More specifically, large and diverse populations of binding molecules for the identification of a further paraptosis-modulating compound will contain any of about $10^4$, $10^5$, $10^6$, $10^7$, $10^8$, $10^9$, $10^{10}$, or more, different molecule species. One skilled in the art will know the approximate diversity of the population of test-compounds sufficient to identify additional paraptosis-modulating compounds useful for practicing the methods of the invention.

Libraries of organic compounds from natural or synthetic sources can be used to identify a paraptosis-modulating compound. These libraries can be generated using combinatorial chemistry techniques well known in the art. For example, a particular pharmacophore can be used as a core compound and several variations of the core compound can be generated in a conventional or iterative process. In addition, a randomly assembled mixture of available related or unrelated compounds can used in the invention. Several libraries of organic compounds are commercially available.

Recombinant libraries of test compounds can be used to identify a paraptosis-modulating compound since large and diverse populations can be rapidly generated and screened via the invention methods. Recombinant libraries of expressed polypeptides useful for identifying a paraptosis-modulating compound can be engineered in a large number of different ways known in the art. Recombinant library methods similarly allow for the production of a large number of test compound populations from naturally occurring repertoires. Whether recombinant or otherwise, essentially any source of test compound population can be used so long as the source provides a sufficient size and diversity of different compounds to identify a paraptosis-modulating compound. If desired, a population of test compounds useful for identifying a paraptosis-modulating compound can be a selectively immobilized to a solid support as described by Watkins et al., *Anal. Biochem.* 256: 169–177 (1998), which is incorporated herein by reference.

A phage expression library in which lysogenic phage cause the release of bacterially expressed binding molecule polypeptides is a specific example of a recombinant library that can be used to identify a paraptosis-modulating compound. In another type of phage expression library, large numbers of potential paraptosis-modulating compounds can be expressed as fusion polypeptides on the periplasmic surface of bacterial cells. Libraries in yeast and higher eukaryotic cells exist as well and are similarly applicable in the methods of the invention. Those skilled in the art will know or can determine what type of library is useful for identifying a paraptosis-modulating compound.

In addition to the methods described above, a paraptosis-modulating compound useful for practicing the invention method can also be identified by using purified polypeptide to produce antibodies, which can serve as neutralizing agents of the invention. For example, antibodies which are specific for SP, caspase-7, caspase-8, caspase-9, JNK1, JNK2 or TRAF2, or another endogenous paraptosis-mediating compound can be used as a paraptosis-modulating compound of the invention and can be generated using methods that are well known in the art. Such paraptosis-modulating compounds can include both polyclonal and monoclonal antibodies against SP, NK1R, a MAPK signaling pathway protein, IGFIR, caspase-7, caspase-8, caspase-9, JNK1, JNK2 or TRAF2, or any endogenous paraptosis-mediating molecule, as well as antigen binding fragments of such antibodies including Fab, F(ab')2, Fd and Fv fragments and the like. In addition, further paraptosis-modulating compounds useful for practicing the methods of the invention encompass non-naturally occurring antibodies, including, for example, single chain antibodies, chimeric antibodies, bifunctional antibodies, complementarity determining region-grafted (CDR-grafted) antibodies and humanized antibodies, as well as antigen-binding fragments thereof.

Methods of preparing and isolating antibodies, including polyclonal and monoclonal antibodies, using peptide immunogens, are well known to those skilled in the art and are described, for example, in Harlow and Lane, *Antibodies: A Laboratory Manual*, Cold Spring Harbor Laboratory Press (1988). Non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference. These and other methods of making, for example, chimeric, humanized, CDR-grafted, single chain, and bifunctional antibodies are well known to those skilled in the art (Hoogenboom et al., U.S. Pat. No. 5,564,332, issued Oct. 15, 1996; Winter and Harris, *Immunol. Today* 14:243–246 (1993); Ward et al., *Nature* 341:544–546 (1989); Harlow and Lane, *Antibodies: A Laboratory Manual* (Cold Spring Harbor Laboratory Press, 1988); Hilyard et al., *Protein Engineering: A Practical Approach* (IRL Press 1992); Borrabeck, *Antibody Engineering*, 2d ed. (Oxford University Press 1995); each of which is incorporated herein by reference).

A paraptosis-modulating compound can be raised using as an immunogen a substantially purified protein, which can be prepared from natural sources or produced recombinantly, or a peptide portion of a paraptosis-mediating molecule including synthetic peptides. A non-immunogenic peptide portion of a paraptosis-mediating molecule can be made immunogenic by coupling the hapten to a carrier molecule such bovine serum albumin (BSA) or keyhole limpet hemocyanin (KLH), or by expressing the peptide portion as a fusion protein. Various other carrier molecules and methods for coupling a hapten to a carrier molecule are well known in the art (see Harlow and Lane, supra, 1988; see, also, Hermanson, *Bioconjugate Techniques*, Academic Press, 1996, which is incorporated herein by reference). As described above, an antibody paraptosis-modulating compound can also be raised against a regulatory molecule that mediates paraptotic activity.

A paraptosis-modulating compound can be labeled so as to be detectable using methods well known in the art (Hermanson, supra, 1996; Harlow and Lane, supra, 1988; chap. 9). For example, a paraptosis-modulating compound can be linked to a radioisotope or therapeutic agent by methods well known in the art. A paraptosis-modulating compound that directly binds to an endogenous paraptosis-mediating molecule linked to a radioisotope or other moiety capable of visualization can be useful to diagnose or stage the progression of a clinical stage of a neurodegenerative condition characterized by the organ or tissue-specific presence or absence of a endogenous paraptosis-mediating molecule.

The invention also provides a method of inhibiting paraptosis or SP-induced paraptosis by preventing the association or interaction of endogenous paraptosis-mediating molecules. For example, a method of identifying a compound that inhibits paraptosis or SP-induced paraptosis by preventing association between molecules in the MAPK signaling pathway can be used in the invention. A method for identifying an agent that alters the association of MAPK pathway proteins, for example, can encompass allowing a MAPK pathway protein such as ERK-2 to bind to a solid support, then adding MEK-1 and an agent to be tested, under conditions suitable for the association of ERK-2 and MEK-1. If desired, the MAPK pathway proteins can be detectably labeled so as to facilitate identification of the association. Control reactions, which contain or lack either, ERK-2, MEK-1, or the agent, also can be performed. Following incubation of the reaction mixture, the amount of ERK-2 that is specifically bound to MEK-1 in the presence of an agent can be determined and compared to the amount of binding in the absence of the agent so that agents that modulate the association can be identified. While described with reference to MAPK pathway proteins, the above methods are applicable for preventing association of any endogenous paraptosis-mediating molecule.

A transcription activation assay such as the two hybrid assay, which can be performed in yeast cells or mammalian cells, allows the identification of protein—protein interactions and, further, can be particularly useful as the basis for a drug screening assay (Fields and Song, *Nature* 340: 245–246 (1989); Fearon et al., *Proc. Natl. Acad. Sci., USA* 89:7958–7962 (1992), each of which is incorporated herein by reference). Such an assay provides the advantage of being performed in cells in culture and, therefore, as compared to an in vitro screening assay, identifies paraptosis-modulating compounds that alter the association of endogenous paraptosis-mediating molecules under more physiological conditions provided by a living cell. Such a paraptosis-modulating compound can be identified by detecting an altered level of transcription of a reporter gene, the expression of which is dependent on the association of paraptosis-mediating molecules, as compared to the level of transcription in the absence of the paraptosis-modulating compound.

Where the identification assay using the two hybrid system is performed in yeast, a potential paraptosis-modulating compound may not be able to cross the yeast cell wall and, therefore, cannot enter the yeast cell to alter a protein—protein interaction. The use of yeast spheroplasts, which are yeast cells that lack a cell wall, can circumvent this problem (Smith and Corcoran, *Current Protocols in Molecular Biology* (ed. Ausubel et al.; Green Publ., NY 1989), which is incorporated herein by reference). In addition, a paraptosis-modulating compound, upon entering a cell, may require "activation" by a cellular mechanism that may not be present in yeast. Activation of a paraptosis-modulating compound can include, for example, metabolic processing of the agent or a modification such as phosphorylation of the agent, which can be necessary to confer activity upon the paraptosis-modulating compound. In this case, a mammalian cell line can be used to screen a panel of agents (Fearon et al., supra, 1992).

The invention further provides a method of identifying a ligand-receptor pair that induces a form of paraptosis in a cell by contacting a first sub-population of cells with a ligand, contacting a second sub-population of cells with the ligand and an agent that blocks a receptor of the ligand, measuring paraptotic cell death in the first and second sub-populations of cells, where increased paraptotic cell death in the first sub-population of cells compared to the second sub-population of cells indicates that the ligand-receptor pair induces a form of paraptosis in the cell. The ligand-receptor pair can induce any form of paraptotic death including paraptosis or SP-induced paraptosis. For example, a first sub-population of neuronal cells can be contacted with SP and a second sub-population of the same neuronal cells can be contacted with SP and a compound that blocks NK1R such as L-732,138 or L-733,060. The level of cell death or paraptotic cell death can be measured in both sub-populations, for example using a trypan blue assay and microscopic evaluation of the cells. An increased level of cell death or paraptotic cell death in the first sub-population of cells that were contacted with SP compared to the second sub-population of cells that were contacted with SP and a NK1R blocker indicates that SP and NK1R are a ligand-receptor pair that induces a form of paraptosis in the cell.

Agents that block a receptor (receptor blockers) can block any function of the receptor. For example, a receptor blocker can block the binding of the ligand to the receptor, the binding of co-factors to the receptor, alter the conformation of the receptor, or block the receptor from interacting with intercellular signaling molecules. A receptor blocker, for example, a receptor antagonist, can be a competitive or non-competitive blocker of the ligand. Generally, an excess of the receptor blocker compared to the ligand is added to ensure that all sites of the receptor are blocked.

The order of addition of the ligand and receptor blocker to the second sub-population of cells can be variable. In some cases, a receptor blocker is added to the cells first followed at a specific time later, for example, 1 minute to 60 minutes, by addition of the ligand. However, in some cases the receptor blocker and ligand can be added at the same time or the blocker can even be added after the addition of the ligand in some cases. The order of addition depends on the type of receptor blocker used and on what is known about the ligand-receptor pair. For example, the on-off rate of the receptor blocker and ligand can be used to determine the best order of addition of the blocker and ligand.

Once a ligand-receptor pair is identified, additional experiments can be done to confirm or characterize the pair. For example, an analogue of the ligand can be used that is known to bind but not activate the receptor. Also, for example, the receptor can be expressed in a cell that does not normally express the receptor to determine if the receptor-ligand pair induces a form of paraptosis in different cell backgrounds. In addition, a mutant receptor, such as an inactive receptor, can be expressed in the cell that does not normally the receptor to determine the role of the receptor in paraptotic processes.

As used herein, the term "ligand" refers to a molecule that can selectively bind to a receptor. The term selectively means that the binding interaction is detectable over non-specific interactions by a quantifiable assay. A ligand can be essentially any type of molecule such as polypeptide, nucleic acid, carbohydrate, lipid, or any organic derived compound. Moreover, derivatives, analogues and mimetic compounds are also intended to be included within the definition of this term. In some cases, a molecule that is a ligand can also be a receptor and, conversely, a molecule that is a receptor can also be a ligand since ligands and receptors are defined as binding partners. For example, an antibody can be defined as a ligand or a receptor.

As used herein, the term "receptor" is intended to refer to a molecule of sufficient size so as to be capable of selectively binding a ligand. Such molecules generally are macromolecules, such as polypeptides, nucleic acids, carbohydrate or lipid. However, derivatives, analogues and mimetic compounds as well as natural or synthetic organic compounds are also intended to be included within the definition of this term. The size of a receptor is not important so long as the receptor exhibits or can be made to exhibit selective binding activity to a ligand. Furthermore, the receptor can be a fragment or modified form of the entire molecule so long as it exhibits selective binding to a desired ligand. For example, if the receptor is a polypeptide, a fragment or domain of the native polypeptide which maintains substantially the same binding selectivity as the intact polypeptide is intended to be included within the definition of the term receptor.

Receptors can include, for example, cell surface receptors such as G protein coupled receptors, integrins, growth factor receptors and cytokine receptors. In addition, cytoplasmic receptors such as steroid hormone receptors and DNA binding polypeptides such as transcription factors and DNA replication factors are likewise included within the definition of the term receptor.

The receptors can be, for example, cell surface receptors that transmit intracellular signals upon binding of a ligand. For example, the G protein coupled receptors span the membrane seven times and couple signaling to intracellular heterotrimeric G proteins. G protein coupled receptors participate in a wide range of physiological functions, including hormonal signaling, vision, taste and olfaction. Moreover, these receptors encompass a large family of receptors, including receptors for acetylcholine, adenosine and adenine nucleotides, β-adrenergic ligands such as epinephrine, angiotensin, bombesin, bradykinin, cannabinoids, chemokines, dopamine, endothelin, histamine, melanocortins, melanotonin, neuropeptide Y, neurotensin, opioid peptides, platelet activating factor, prostanoids, serotonin, somatostatin, tachykinin and SP, thrombin and vasopressin, among others.

Other cell surface receptors have intrinsic tyrosine kinase activity and include growth factor or hormone receptors for ligands such as platelet-derived growth factor, epidermal growth factor, insulin, insulin-like growth factor, hepatocyte growth factor, and other growth factors and hormones. In addition, cell surface receptors that couple to intracellular tyrosine kinases include cytokine receptors such as those for the interleukins and interferons.

Integrins are cell surface receptors involved in a variety of physiological processes such as cell attachment, cell migration and cell proliferation. Integrins mediate both cell-cell and cell-extracellular matrix adhesion events. Structurally, integrins consist of heterodimeric polypeptides where a single α chain polypeptide noncovalently associates with a single β chain. In general, different binding specificities are derived from unique combinations of distinct α and β chain polypeptides. For example, vitronectin binding integrins contain the $\alpha_v$ integrin subunit and include $\alpha_v\beta_3$, $\alpha_v\beta_1$, and $\alpha_v\beta_5$, all of which exhibit different ligand binding specificities.

The invention provides a method of inducing SP-induced paraptosis in a cell by contacting the cell with an effective amount of SP, where the effective amount of SP induces SP-induced paraptosis in the cell. In addition, the invention provides a method of inducing SP-induced paraptosis in a cell that expresses neurokinin receptor 1 (NK1R) by contacting the cell with an effective amount of SP, where the effective amount of SP induces SP-induced paraptosis in the cell. As described further above, the cell can be a neuronal cell or a non-neuronal cell.

The invention further provides a method of increasing SP-induced paraptosis in a cell by contacting the cell with an effective amount of a compound that modulates SP-induces paraptosis. For example, the invention provides a method of increasing SP-induced paraptosis in a cell by contacting the cell with an effective amount of a compound that modulates SP-induces paraptosis identified by (a) contacting a population of cells with an effective amount of substance P to induce SP-induced paraptosis; (b) contacting a first sub-population of the cells with a test-compound, and a second sub-population of the cells with a control-compound; and (c) comparing the amount of cell death between the first and second sub-populations of cells, where a difference in the amount of cell death between the first and second sub-populations of cells indicates that the test-compound is a compound that modulates SP-induced paraptosis.

The invention further provides a method of decreasing SP-induced paraptosis in a cell by contacting the cell with an effective amount of a compound that modulates SP-induces paraptosis. For example, the invention provides a method of decreasing SP-induced paraptosis in a cell by contacting the cell with an effective amount of a compound that modulates SP-induces paraptosis by (a) contacting a population of cells with an effective amount of substance P to induce SP-induced paraptosis; (b) contacting a first sub-population of the cells with a test-compound, and a second sub-population of the cells with a control-compound; and (c) comparing the amount of cell death between the first and second sub-populations of cells, where a difference in the amount of cell death between the first and second sub-populations of cells indicates that the test-compound is a compound that modulates SP-induced paraptosis.

The paraptosis-modulating compounds, including compounds that modulate SP-induced paraptosis, that inhibit paraptotic cell death taught herein are useful in the invention methods of treating or reducing the severity of a condition associated with excessive cell death, for example, an ischemic condition such as stroke or myocardial infarction; or a neurodegenerative condition. Conversely, paraptosis-modulating compounds that induce paraptotic cell death are useful in the invention methods of reducing the severity of a condition associated with excessive cell accumulation, for example, a neoplastic condition or an autoimmune condition. A paraptosis-modulating compound can modulate paraptotic activity by binding to an endogenous paraptosis-mediating molecule, to a regulatory molecule that modulates the activity or expression of an endogenous paraptosis-mediating molecule, or to a gene region that controls expression of an endogenous paraptosis-mediating molecule. For example, a paraptosis-modulating compound useful for practicing the claimed invention can be an antibody against a regulator molecule that modulates expression or activity of an endogenous paraptosis-mediating molecule. Alternatively, it may be desired to use populations of random peptide populations to identify further paraptosis-modulating compounds. Those skilled in the art will know or can determine what type of approach and what type of paraptosis-modulating compound is appropriate for practicing the methods of the invention.

The invention therefore provides a method of treating a condition associated with excessive cell accumulation by administering to a subject in need of such treatment an effective amount of a compound selected from the group consisting of ceramide, Tumor Necrosis Factor (TNF), caspase-7, caspase-8, α-amino-3-hydroxy-5-methyl-4-isoxazole proprionic acid (AMPA), kainic acid and glutamic acid, where the effective amount of the compound induces paraptotic cell death.

The invention further provides a method of treating a condition associated with excessive cell accumulation by administering to a subject in need of such treatment an effective amount of SP, where the effective amount of the compound induces SP-induced paraptosis.

In addition, the invention provides a method of treating a condition associated with excessive cell accumulation by administering to a subject in need of such treatment an effective amount of a compound that modulates SP-induced paraptosis (paraptosis-modulating compound) where the effective amount of the compound increases SP-induced paraptosis. For example, the invention provides a method of treating a condition associated with excessive cell accumulation by administering to a subject in need of such treatment an effective amount of a compound identified from the methods described herein such as, for example, (a) contacting a population of cells with an effective amount of substance P to induce SP-induced paraptosis; (b) contacting a first sub-population of the cells with a test-compound, and a second sub-population of the cells with a control-compound; and (c) comparing the amount of cell death between the first and second sub-populations of cells, where a difference in the amount of cell death between the first and second sub-populations of cells indicates that the test-compound is a compound that modulates SP-induced paraptosis.

In a separate embodiment, the invention provides a method of treating a condition associated with excessive cell death comprising administering to a subject in need of such treatment an effective amount of a compound selected from the group consisting of Alg-2-interacting protein 1 (AIP-1), Jun N-terminal kinase 1 (JNK1) neutralizing agent, Jun N-terminal kinase 2 (JNK2) neutralizing agent, TNF Receptor-Associated Factor 2 (TRAF2) neutralizing agent, orthophenanthroline and the JNK inhibitor SP 600125, wherein the effective amount of the compound inhibits paraptotic cell death.

In addition, the invention provides a method of treating a condition associated with excessive cell death by administering to a subject in need of such treatment an effective amount of a compound that modulates SP-induced paraptosis (paraptosis-modulating compound) where the effective amount of the compound decreases SP-induced paraptosis. For example, the invention provides a method of treating a condition associated with excessive cell death by administering to a subject in need of such treatment an effective amount of a compound identified from the methods described herein such as, for example, (a) contacting a population of cells with an effective amount of substance P to induce SP-induced paraptosis; (b) contacting a first sub-population of the cells with a test-compound, and a second sub-population of the cells with a control-compound; and (c) comparing the amount of cell death between the first and second sub-populations of cells, where a difference in the amount of cell death between the first and second sub-populations of cells indicates that the test-compound is a compound that modulates SP-induced paraptosis.

As used herein, the term "treating" when used in reference to a pathological condition is intended to refer to any detectable beneficial therapeutic effect on the pathological condition of the subject being treated. The beneficial effect can be evidenced, for example, by a delayed onset of clinical symptoms, a reduction in severity of some or all clinical symptoms of the condition, a slower progression of the condition, a reduction in the number of relapses of the condition, a reduction in the number or activity of pathogenic cells, an improvement in the overall health or well-being of the individual, or by other parameters known in the art that are specific to the particular condition.

As used herein, the term "autoimmune condition" refers to a condition characterized by an immune response against the body's own tissues. Autoimmune conditions develop when the immune system destroys normal body tissues caused by a hypersensitivity reaction similar to allergies, where the immune system reacts to a substance that it normally would ignore. The methods described herein for inducing paraptotic cell death can be used to treat a subject where it is desirable to induce cell death in the immunoeffector cells that mediate the autoimmune condition.

As used herein, the term "ischemic condition" refers to a condition in which blood flow is insufficient to support the metabolic demand of a tissue, often due to stenosis or occlusion of a blood vessel. For example, in myocardial ischemia the blood flow to the heart is insufficient to support the metabolic demand of the heart, resulting in myocardial hypoxia and accumulation of waste metabolites, most often due to atherosclerotic disease of the coronary arteries. The term "myocardial infarction," as used herein, refers to damage to the heart muscle caused by stenosis of one or more of the coronary arteries. The term "stroke," as used herein refers to a condition that occurs when stenosis of blood vessels carrying oxygen and other nutrients to a specific part of the brain fails to reach that part of the brain such that the brain oxygen supply is cut off resulting in brain damage.

As used herein, the term "neural cell death" disease or disorder or "neurodegenerative condition" refers to a condition that is characterized by increased or accelerated neural cell death. Neural cell death or neurodegenerative diseases include diseases such as retinal degeneration, Huntington's Disease (HD), Parkinson's Disease (PD) and Alzheimer's Disease (AD) as well as other diseases associated with the loss of neural cells including, for example, stroke, trauma, global ischemia, hypoxis, seizure-induced excitotoxicity. The methods described herein for inhibiting paraptotic cell death can be used to treat an individual having a condition characterized by a pathologically elevated level of a form of paraptosis, such as occurs in neuronal cells in patients with neurodegenerative conditions, including Parkinson's disease, Huntington's disease, Alzheimer's disease and the encephalopathy that occurs in AIDS patients. Exemplary compounds contemplated for inhibiting forms of paraptosis include paraptosis-modulating compounds identified by the invention methods and, for example, a MAPKK inhibitor such as PD 98059.

As described herein, modulation of forms of paraptosis can be a therapeutic strategy for treatment of a variety of neural cell death disorders as well as neoplastic pathologies. As such, administration of a compound that inhibits forms of paraptosis can lead to a reduction in the severity of a neural cell death disorder.

Neural cell death or neurodegenerative diseases such as AD, PD, ALS, and HD result in the death of particular populations of neurons. For example, ALS attacks motor neurons while PD results in the loss of dopaminergic neurons of the *substantia nigra*. Different molecules and cell death mechanisms have been implicated in each of these neural cell death disease, for example, abnormal processing of a beta amyloid protein in AD, and expansion of a trinucleotide repeat in HD, however all of these diseases eventually result in neuronal cell death. The types of neuronal cell death occurring in these diseases appears, in part, to be distinct from necrosis and apoptosis.

Methods which result in the inhibition of paraptotic cell death can be used, for example, to treat neural cell death diseases. For example, the methods and compounds of the invention can be used in the treatment of Huntington's disease, ALS, Alzheimer's disease, Parkinson's disease, trauma, stroke, and epilepsy. Since neural cell death diseases can exhibit more than one form of cell death, it is contemplated that the methods and compounds of the invention can also be used as part of a combination therapy that further includes an effective amount of a compound known to reduce other forms of cell death, such as, for example, apoptotic cell death.

As described herein, paraptotic cell death and apoptosis represent two separate programs of cell death that are induced via distinct molecular pathways, but may be induced simultaneously by a single insult or agent. Consequently, the invention method of treating a condition associated with excessive cell accumulation can be practiced by administering to a subject a combination therapy that consists of an effective amount of a compound selected from the group consisting of SP, ceramide, Tumor Necrosis Factor (TNF), caspase-7, caspase-8, α-amino-3-hydroxy-5-methyl-4-isoxazole proprionic acid (AMPA), kainic acid and glutamic acid to induce paraptotic cell death and an effective amount of a compound known to induce apoptotic cell death. Compounds known to induce apoptotic cell death include several agents including chemotherapeutic agents that are known in the literature. Chemotherapeutic agents include, for example, anthracyclins, alkylating agents, vinca alkaloids, nucleotide analogs, cis-platinum, doxorubicin, taxol, tamoxifen, methotrexate and mitomycin C.

Methods which result in the increase in paraptosis can be used, for example, to treat neoplastic conditions. For example, the methods and compounds of the invention can be used in the treatment of neoplastic conditions that involve neuronal cells in the nervous system or at other sites in the body. It is contemplated that the methods and compounds of the invention can also be used in combination with other therapies to treat a neoplastic condition. For example, a paraptosis-modulating compound identified by methods of the invention can be used as part of a combination therapy that further includes an effective amount of a compound known to induce other forms of cell death, such as, for example, apoptotic cell death.

Induction of paraptotic cell death in neoplastic cells that are sensitive to paraptosis or SP-induced paraptosis can lead to a reduction in the severity of a neoplastic disorder. For example, the induction of paraptotic cell death in neoplastic cells that express NK1R or that are responsive to SP can reduce the severity of a neoplastic disorder resulting from these neoplastic cells. Neoplastic cells that are sensitive to paraptotic cell death can be present in the nervous system, such as cortical neurons, or outside the nervous system, such as in organs enervated by neurons from the nervous system. In addition, paraptosis can be induced in non-neuronal neoplastic cells. Neoplastic cells outside the nervous system, such as tumors with neuroendocrine features that express peptide receptors and respond to neuropeptide stimulation, as, for example, many small cell lung cancers (SCLC), non-SCLCs, prostate, breast, gastrointestinal cancers (Chan et al., *Proc. Natl. Acad. Sci, USA* 99:4608–4613 (2002)) can be sensitive to paraptotic cell death. Furthermore, for example, a neoplastic condition such as a tumor that is sensitive to paraptotic cell death can originate outside of the nervous system and metastasize to the nervous system.

Several types of neoplastic conditions are known within the nervous system. Neuroepithelial tumors of the CNS include, for example, neuronal and mixed neuronal-glial tumors such as gangliocytomas, gangliogliomas, central neurocytomas, and olfactory neuroblastomas. Tumors with neuroblastic or glioblastic elements include medulloepitheliomas, primary neuroectrodermal tumors, neuroblastomas, retinoblastomas, and ependymoblastomas. Astrocytic tumors include astrocytomas, glioblastomas, and pilocytic astrocytomas. Several tumors in the nervous system have been characterized and classified, for example, in the World Health Organization (WHO) classification of tumors affecting the central nervous system.

Similarly, the invention method of treating a condition associated with excessive cell death can be practiced by administering to a subject a combination therapy that consists of an effective amount of a compound selected from the group consisting of Alg-2-interacting protein 1 (AIP-1), MEK 1 and MEK 2 inhibitors, Jun N-terminal kinase 1 (JNK1) neutralizing agent, Jun N-terminal kinase 2 (JNK2) neutralizing agent, TNF Receptor-Associated Factor 2 (TRAF2) neutralizing agent, ortho-phenanthroline and the JNK inhibitor SP 600125 to inhibit paraptotic cell death and an effective amount of a compound known to inhibit apoptotic cell death. Compounds known to inhibit (decrease) apoptotic cell death are well known in the art and include, for example, dominant negative caspase-3 and zVAD.fmk.

A paraptosis-modulating compound of the invention can be useful in the invention methods for treatment of a condition characterized by increased or decreased paraptotic cell death. Various conditions are characterized by an increased or decreased level of forms of paraptosis as compared to the normal level of paraptotic processes for a particular population of cells. For example, decreased levels of forms of paraptosis are associated with neoplastic conditions, including cancer, where a tumor forms amidst otherwise normal cells in a tissue or organ. In addition, increased levels of forms of paraptosis are associated with a number of neurodegenerative conditions including stroke, trauma, global ischemia, hypoxia, seizure-induced excitotoxicity, and certain neurodegenerative diseases. As set forth herein, the therapeutic methods of the invention are useful for treatment or reduction in severity of conditions associated with either excessive cell accumulation or excessive cell death due to a lack of homeostasis of paraptotic pathways.

As disclosed herein, paraptosis or SP-induced parpatosis can be modulated by contacting the appropriate cell or cell population with a paraptosis-modulating compound, for example, an inducing compound such as ceramide, Tumor Necrosis Factor (TNF), caspase-7, caspase-8, α-amino-3-hydroxy-5-methyl-4-isoxazole proprionic acid (AMPA), kainic acid and glutamic acid; or a paraptosis-inhibiting compound such as Alg-2-interacting protein 1 (AIP-1), Jun N-terminal kinase 1 (JNK1) neutralizing agent, Jun N-terminal kinase 2 (JNK2) neutralizing agent, TNF Receptor-Associated Factor 2 (TRAF2) neutralizing agent, ortho-phenanthroline, MEK and ERK inhibitors, NK1R signaling blockers, and the JNK inhibitor SP 600125. Such paraptosis-modulating compounds, therefore, are useful as medicaments for treating a pathology characterized, in part, by aberrant paraptotic cell death. The skilled artisan will recognize the broader usefulness of paraptosis-modulating compounds for therapeutic treatment of conditions characterized by aberrant levels of paraptotic cell death.

Paraptosis can be induced in a cellular system by overexpressing, for example, caspase-7, caspase-8 or caspase-9, the latter in the presence of an apoptosis inhibitor. Caspase-7 and caspase-8 expression induces both apoptotic and paraptotic cell death. Subsequent to the induction of paraptosis, a co-immunoprecipitation assay or similar immunoassay can be performed to identify further compounds that are associated with caspase-9 in paraptotic cells and, consequently, are candidate paraptosis-modulating compound. The paraptosis-modulating activity of the caspase-9-co-immunoprecipitating compound can be verified using the methods known in the art.

The paraptosis-modulating compounds, including compounds that modulate SP-induced parpatosis, taught herein and useful for practicing the methods of the invention can be formulated and administered by those skilled in the art in a manner and in an amount appropriate for the condition to be treated; the rate of disease progression; severity of symptoms, the weight, gender, age and health of the subject; the biochemical nature, bioactivity, bioavailability and side effects of the particular compound; and in a manner compatible with concurrent treatment regimens. An appropriate amount and formulation for decreasing the severity of a neoplastic condition, autoimmune condition, ischemic condition, neurodegenerative condition in humans can be extrapolated from credible animal models known in the art of the particular condition. It is understood, that the dosage of a paraptosis-modulating compound may have to be adjusted based on the binding affinity of the paraptosis-modulating compound for a second compound, such that a lower dose of a paraptosis-modulating compound exhibiting significantly higher binding affinity can be administered compared to the dosage necessary for a paraptosis-modulating compound with lower binding affinity.

The total amount of a paraptosis-modulating compound can be administered as a single dose or by infusion over a relatively short period of time, or can be administered in multiple doses administered over a more prolonged period of time. Such considerations will depend on a variety of case-specific factors such as, for example, in case of a neurodegenerative disease it will depend on whether the disease category is characterized by acute episodes or gradual deterioration. For example, for a subject affected with chronic deterioration the paraptosiss-modulating compound can be administered in a slow-release matrix, which can be implanted for systemic delivery or at the site of the target tissue. Contemplated matrices useful for controlled release of therapeutic compounds are well known in the art, and include materials such as DEPOFOAM™, biopolymers, micropumps, and the like.

The paraptosis-modulating compounds can administered to the subject by any number of routes known in the art including, for example, systemically, such as intravenously or intraarterially. A paraptosis-modulating compound can be provided, for example, in the form of isolated and substantially purified polypetides and polypeptide fragments in pharmaceutically acceptable formulations using formulation methods known to those of ordinary skill in the art. These formulations can be administered by standard routes, including, for example, topical, transdermal, intraperitoneal, intracranial, intracerebroventricular, intracerebral, intravaginal, intrauterine, oral, rectal or parenteral (e.g., intravenous, intraspinal, subcutaneous or intramuscular) routes. In addition, a paraptosis-modulating compound can be incorporated into biodegradable polymers allowing for sustained release of the compound useful for reducing the severity of a neoplastic condition or neurodegenerative condition. Biodegradable polymers and their use are described, for example, in Brem et al., *J. Neurosurg.* 74:441–446 (1991), which is incorporated herein by reference.

A paraptosis-modulating compound can be administered as a solution or suspension together with a pharmaceutically acceptable medium. Such a pharmaceutically acceptable medium can be, for example, sterile aqueous solvents such as sodium phosphate buffer, phosphate buffered saline, normal saline or Ringer's solution or other physiologically buffered saline, or other solvent or vehicle such as a glycol, glycerol, an oil such as olive oil or an injectable organic ester. A pharmaceutically acceptable medium can additionally contain physiologically acceptable compounds that act, for example, stabilize the paraptosis-modulating compound, increase its solubility, or increase its absorption. Such physiologically acceptable compounds include, for example, carbohydrates such as glucose, sucrose or dextrans; antioxidants such as ascorbic acid or glutathione; receptor mediated permeabilizers, which can be used to increase permeability of the blood-brain barrier; chelating agents such as EDTA, which disrupts microbial membranes; divalent metal ions such as calcium or magnesium; low molecular weight proteins; lipids or liposomes; or other stabilizers or excipients. Those skilled in the art understand that the choice of a pharmaceutically acceptable carrier depends on the route of administration of the compound containing the paraptosis-modulating compound and on its particular physical and chemical characteristics.

Formulations suitable for parenteral administration include aqueous and non-aqueous sterile injection solutions such as the pharmaceutically acceptable mediums described above. The solutions can additionally contain, for example, buffers, bacteriostats and solutes which render the formulation isotonic with the blood of the intended recipient. Other formulations include, for example, aqueous and non-aqueous sterile suspensions which can include suspending agents and thickening agents. The formulations can be presented in unit-dose or multi-dose containers, for example, sealed ampules and vials, and can be stored in a lyophilized condition requiring, for example, the addition of the sterile liquid carrier, immediately prior to use. Extemporaneous injection solutions and suspensions can be prepared from sterile powders, granules and tablets of the kind previously described.

For applications that require the compounds and compositions to cross the blood-brain barrier, formulations that increase the lipophilicity of the compound are particularly desirable. For example, the paraptosis-modulating compound can be incorporated into liposomes (Gregoriadis, *Liposome Technolosv*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer.

A paraptosis-modulating compound can also be prepared as nanoparticles. Adsorbing peptide compounds onto the surface of nanoparticles has proven effective in delivering peptide drugs to the brain (see Kreuter et al., *Brain Res.* 674:171–174 (1995)). Exemplary nanoparticles are colloidal polymer particles of poly-butylcyanoacrylate with paraptosis-modulating compound adsorbed onto the surface and then coated with polysorbate 80.

Image-guided ultrasound delivery of a paraptosis-modulating compound through the blood-brain barrier to seiected locations in the brain can be utilized as described in U.S. Pat. No. 5,752,515. Briefly, to deliver a paraptosis-modulating compound past the blood-brain barrier a selected location in the brain is targeted and ultrasound used to induce a change detectable by imaging in the central nervous system (CNS) tissues and/or fluids at that location. At least a portion of the brain in the vicinity of the selected location is imaged, for example, via magnetic resonance imaging (MRI), to confirm the location of the change. A paraptosis-modulating compound in the patient's bloodstream can be delivered to the confirmed location by applying ultrasound to effect opening of the blood-brain barrier at that location and, thereby, to induce uptake of the paraptosis-modulating compound.

In addition, polypeptides called receptor mediated permeabilizers (RMP) can be used to increase the permeability of the blood-brain barrier to molecules such as therapeutic agents or diagnostic agents as described in U.S. Pat. Nos. 5,268,164; 5,506,206; and 5,686,416. These receptor mediated permeabilizers can be intravenously co-administered to a host with molecules whose desired destination is the cerebrospinal fluid compartment of the brain. The permeabilizer polypeptides or conformational analogues thereof allow therapeutic agents to penetrate the blood-brain barrier and arrive at their target destination.

In current treatment regimes for neoplastic conditions, autoimmune conditions, ischemic conditions as well as for neurodegenerative conditions, more than one compound is often administered to an individual for management of the same or different aspects of the disease. Similarly, in the methods of the invention a paraptosis-modulating compound can advantageously be formulated with a second therapeutic compound such as an apoptosis-modulating compound, an anti-inflammatory compound, an immunosuppressive compound or any other compound that manages the same or different aspects of the disease. Such compounds include, for example, methylprednisolone acetate, dexamethasone and betamethasone. Contemplated methods of treating or reducing the severity of a neoplastic conditions, autoimmune conditions, ischemic conditions as well as for neurodegenerative conditions, include administering a paraptosis-modulating compound alone, in combination with, or in sequence with, such other compounds. Alternatively, combination therapies can consist of fusion proteins, where the paraptosis-modulating compound is linked to a heterologous protein, such as a therapeutic protein.

It is understood that modifications which do not substantially affect the activity of the various embodiments of this invention are also included within the definition of the invention provided herein. Accordingly, the following examples are intended to illustrate but not limit the present invention.

EXAMPLE I

Inducers of Paraptosis

This example demonstrates the identification of agents capable of inducing paraptotic cell death.

Human embryonic kidney 293T cell line cells were used to assay for inducers and inhibitors of paraptosis. These cells were cultured in high glucose DMEM (Life Technologies) supplemented with 10% FBS (Sigma) and 1% penicillin/streptomycin (Life Technologies). The cultures were incubated at 37° C. in 95% air 5% carbon dioxide with 95% humidity.

Rat neuronal primary cell cultures were also used to assay for inducers and inhibitors of paraptosis. Briefly, primary striatal, cortical and hippocampal cultures were prepared from 17-day-old Sprague-Dawley rat embryos (B&K). The tissue was dissected, minced and trypsinized for five minutes using 0.25% trypsin (Cell Grow). After the addition of 10% horse serum (Life Technologies) to inhibit the trypsin, the cell suspension was triturated 15–20 times with a 10 ml syringe and centrifuged for five minutes at 800×g. The pellet was resuspended in MEM-PAK (UCSF Cell Culture facility), supplemented with 2.02 gm glucose, 2 mM GLUTAMAX™ (Life Technologies) and penicillin/streptomycin (100 U/ml). The suspension was filtered through a 70 mm cell strainer and the final culture medium contained 5% horse serum. Subsequently, $3-4\times10^5$ cells per $Cm^2$ were seeded onto either poly-D-lysine precoated 8-well chamber slides (Becton-Dickson Labware) or 96 well plates precoated with 50 mg/ml of poly-D-lysine (Sigma) in water. After 30 minutes of incubation time, unattached cells were removed together with the medium and replaced with glucose enriched MEM-PAK plus 5% horse serum. The cultures were then incubated at 37° C. in 95% air 5% carbon dioxide with 95% humidity. Cultures were used for experiments between day 1 and day 7 when glial contamination was at a minimum.

Subsequently, compounds were added to 293T cells and/or rat neuronal primary cell culture cells in order to determine if the compounds could induce paraptosis. Cell death was assayed using the lactate dehydrogenase (LDH) assay, in which the relative amount of enzyme released from dying cells in the medium is measured by following the disappearance of nicotinamide adenine dinucleotide, reduced form (NADH) in the following reaction: pyruvate+NADH <–>$NAD^+$+ lactate. Briefly, 50 µl of culture medium for either 293T cells or 100 µl of culture medium for neuronal primary culture were dispensed in a 96 well plate to which 100 µl of a solution consisting of 5 mg of NADH dissolved in 20 ml of PBS and 0.5 ml of 100 mM NaPyruvate. NADH disappearance was assessed by kinetic photmetric readings at a 340 nm wavelength at 19 minute intervals over a period of 2 hours and 30 minutes.

The following compounds were found to induce paraptosis when used at the concentrations indicated below:

1. C2 ceramide(N-Acetyl-D-sphingosine) used at 15–100 µM in both 293T cells and rat neuronal primary culture cells.
2. Tumor Necrosis Factor-α used at 1-10 ng/ml in 293T cells.
3. AMPA (alpha-amino-3-hydroxy-5-methyl-4-isoxazolepropionic acid) at 35–500 µM in rat neuronal primary cell cultures.
4. Kainic Acid (2-Carboxy-3-carboxymethyl-4-isopropenylpyrrolidine) at 35–500 µM in rat neuronal primary cell cultures.
5. Glutamic Acid ((S)-2-aminopentanedioic acid) at 50–500 µM in rat neuronal primary cell cultures.

In addition, procaspase-7 and procaspase-8 were also able to induce paraptosis when expressed in 293T cells. Constructs of pcDNA3 containing procaspase-7 or procaspase-8 were transiently transfected into 293T cells using Lipofect-Amine (GIBCO-BRL) according to the manufacturer's instructions. Briefly, $1\times10^6$ 293T cells were seeded in 6 cm dishes, and transfected the next day using a ratio of DNA: Lipofect-Amine of 1 µg:5 µl. Transfection efficiency was 60–80% for 293T cells, as determined by X-gal staining after transfection of a β-galactosidase construct.

EXAMPLE II

Inhibitors of Paraptosis

This example demonstrates the identification of agents capable of inhibiting paraptotic cell death.

Paraptosis was induced in 293T cells by expressing the intracellular domain of the insulin-like growth factor I receptor (IGFIR-IC) in these cells using transient transfection as described above.

Test compounds were added to IGFIR-IC transfected 293T cells at the time of transfection. The copper chelator, 1-10-phenantroline (ortho-phenantroline) was able to inhibit IGFIR-IC induced paraptosis when added to transfected 293T cells at a concentration of 50 nM. In addition, H89, an inhibitor of protein kinase A, was able to inhibit IGFIR-IC induced paraptosis when added at a concentration of 10–20 µM. Furthermore, 1–10-phenantroline was able to inhibit paraptosis induced by caspase 8 or caspase 9.

In addition, AIP-1 (Alg-2 interacting protein 1) and a dominant negative mutant of TRAF2 were able to inhibit IGFIR-IC induced paraptosis when co-transfected with the IGFIR-IC construct. The TRAF2 dominant negative mutant contains a deletion of the amino terminal 271 amino acids of the protein. The ratio of IGFIR-IC:AIP1 and IGFIR-IC: TRAF2DN was 1:3. Furthermore, antisense oligonucleotide constructs for JNK1 or JNK2 were able to inhibit IGFIR-IC induced paraptosis in 293T cells. Antisense oligonucleotide constructs for JNK1 or JNK2 (50–100 nM) were transfected into 293T cells one day before transfection with the IGFIR-IC construct. For all inhibition assays, cell viability was measured using the LDH assay.

EXAMPLE III

A Ligand-Receptor Pair that Triggers a Non-Apoptotic Form of Programmed Cell Death This example demonstrates that substance P (SP) can induce a form of paraptosis through the neurokinin 1 receptor (NK1R).

Striatal, cortical, and hippocampal neurons were sensitive to micromolar concentrations of SP 48 hours after exposure to SP (FIG. 6A) whereas fibroblasts were resistant to micromolar concentrations of SP. In addition, these neurons were sensitive to nanomolar concentrations of SP seven days after exposure (FIG. 6B). Note that SP was added only once at the beginning of the experiment.

Figure 7A:
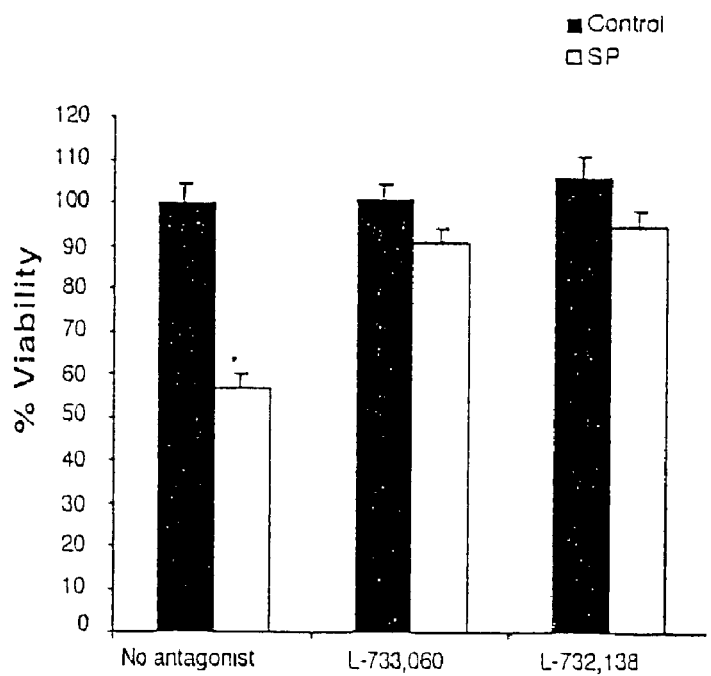
FIG. 7A shows the percentage of viability of striatal cells treated with NK1R antagonists.

The toxicity of SP observed with neuronal cells in comparison to fibroblasts was receptor-dependent, since the L form of SP induced cell death while the D form of SP had no effect on cell death (FIG. 6A). In order to determine if the neurokinin 1 receptor (NK1R) was the mediator of SP-induced neuronal cell death, two different antagonists for NK1R, L-732,138 which is a competitive antagonist, and L-733,060 which is a non-peptide antagonist, were added to the neuronal cultures along with the SP. Both molecules inhibited SP-induced cell death indicating that SP-induced neurotoxicity is mediated, at least in part, by NK1R (FIG. 7A).

SP-Induced Cell Death is Non-Necrotic and Non-Apoptotic

In order to distinguish between an active cell death program and a passive cell death process, SP-induced cell death was evaluated in the presence of the transcription inhibitor actinomycin D and the translation inhibitor cyclohexamide. SP-induced cell death was prevented in the presence of actinomycin D and cyclohexamide indicating that the cell death was an active instead of a passive process (FIG. 7B).

Figure 7B:
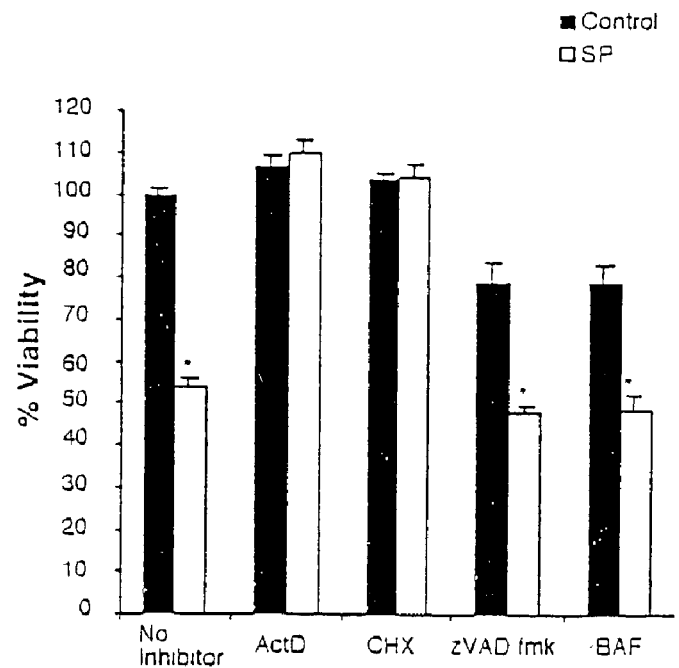
FIG. 7B shows the percentage of viability of striatal cells treated with the indicated compounds.

In addition, SP-induced cell death was not inhibited by the broad-spectrum caspase inhibitors zVAD.fmk and Box-aspartyl.fmk (BAF) indicating that this form of cell death differs from apoptosis (FIG. 7B). Furthermore, morphological studies showed that cells undergoing SP-induced cell death had a phenotype that differed from apoptosis. For example, DAPI staining demonstrated no nuclear fragmentation in cells undergoing SP-induced cell death, although some degree of chromatin condensation occurred. In addition, annexin-V staining showed no evidence for phosphatidylserine flipping in cells undergoing SP-induced cell death. Furthermore, membrane bleb formation or apoptotic body formation were not detected.

NK1R Can Mediate Non-apoptotic Cell Death

As described above, antagonists of NK1R blocked SP-induced neuronal cell death, indicating that NK1R can mediate this type of cell death. It was conceivable that this cell death may require both NK1R and some neuron-specific factor or factors. In order to determine whether NK1R-mediated cell death requires neuron-specific factors, NK1R was expressed in 293T human embryonic kidney cells, which do not express endogenous NK1R. The 293T cell line is resistant to SP-induced cell death even at millimolar concentrations of SP. However, when 293T cells are transfected with NK1R, they become sensitive to SP at nanomolar concentrations and display the same cell death morphology that was observed in primary neurons. For example, the cells rounded up but demonstrated no bleb formation, apoptotic body formation, cell shrinkage or nuclear fragmentation. Instead, electron microscopic analysis revealed swelling and vaculolation. Furthermore, Annexin-V staining was negative in NK1R-mediated death of 293T cells whereas controls tranfected with a Bax expression construct demonstrated clear bleb formation and Annexin-V staining. Similarly, TUNEL (TdT-mediated dUTP Nick-End Labeling) staining to detect DNA fragmentation was negative for NK1R-mediated cell death while control cells expressing Bax developed a positive signal.

Since SP had been shown to display toxicity toward bacteria and mitochondria (del Rio et al., *FEBS Lett.* 494: 213–219 (2001)), it was still possible that the mediation of SP-induced death by NK1R was due to internalization of SP and subsequent mitochondrial toxicity, rather than resulting from the triggering of a signal cascade mediated by NK1R. Therefore, neurokinin A and SP 6–11, which are NK1R agonists that do not exhibit mitochondrial toxicity, were evaluated. These molecules were able to induce cell death as well as SP indicating that NK1R mediates SP-induced neuronal cell death by a mechanism independent of direct mitochondrial damage.

Figure 8A:
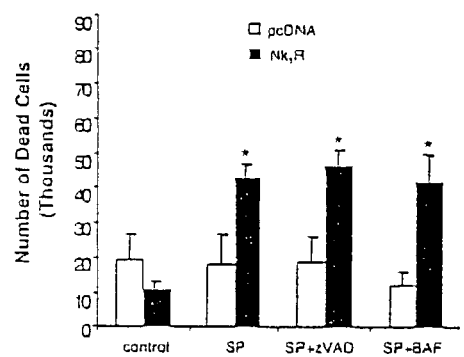
FIG. 8A shows the viability of cells transfected with pcDNA3.1 or a NK1R construct and treated with caspase inhibitors.
Figure 8B:
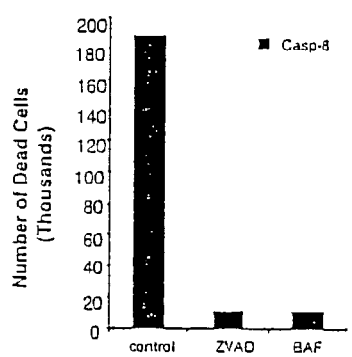
FIG. 8B shows the viability of caspase-8 transfected cells treated with caspase inhibitors.
Figure 8C:
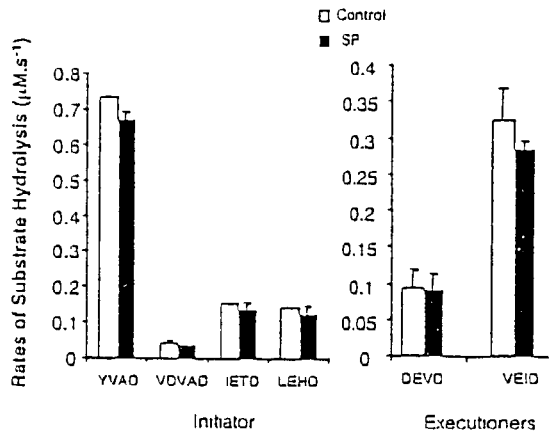
FIG. 8C shows the rate of substrate hydrolysis for initiator or executioner caspases in the presence or absence of SP.
Figure 8D:
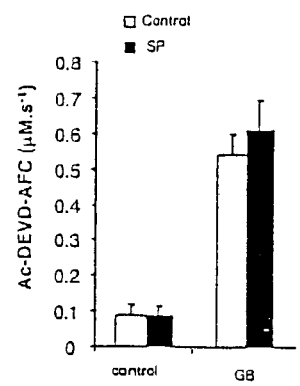
FIG. 8D shows the rate of substrate hydrolysis in the presence or absence of granzyme B and SP.
Figure 9:
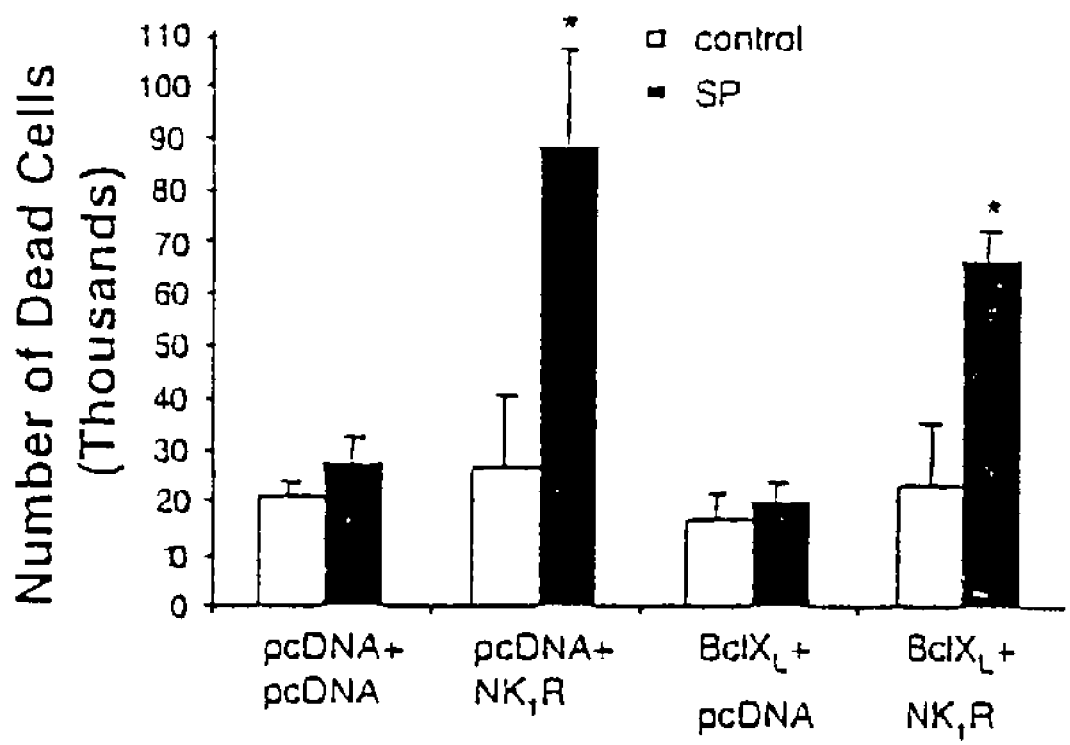
FIG. 9 shows the viability of cells transfected with the indicated plasmids followed by growth in the presence or absence of SP.

As described above, the caspase inhibitors zVAD.fmk and BAF did not inhibit NK1R-mediated cell death in neurons. A similar lack of effect in 293T cells was observed while the apoptosis induced by over-expression of caspase-8 was completely abolished, indicating that the inhibitors were effective (FIGS. 8A and B). Accordingly, no hydrolysis of substrates for either "initiator" caspase-1-2, -8, -9 and 10, or "executioner" caspases-3, -6 and -7 was detected (FIG. 8C). It has been demonstrated that procaspase-3 is present in 293T cells (Stennicke et al., *J. Biol. Chem.* 273:27084–27090 (1998)) and that it is activated by the serine protease granzyme B (Atkinson et al., *J. Biol. Chem.* 273:21261–21266 (1998)). To ensure that the lack of DEVDase activation was not simply due to the lack of activatable procaspase-3, granzyme B was added to each cytosolic extract of 293T cells transfected with NK1R, treated (or not) with SP. The addition of granzyme B activated the procaspase-3, as shown by a 7-fold increase of DEVDase activity, whereas no significant difference was observed in response to SP stimulation (FIG. 8D). These results indicate that the lack of DEVD (SEQ ID NO:1) cleavage during SP-induced cell death was not due to the presence of a nonfunctional procaspase-3. The activation of other endopeptidases was also tested, such as calpains (requiring micromolar or millimolar concentrations of calcium) and the chymotrypsin-like activity of the proteasome, and no significant effect on the rates of substrate hydrolysis was detected. We found further that Bcl-xL expression did not inhibit NK1R-mediated cell death (P=0.486 by ANOVA test) (FIG. 9).

The following techniques were used in the above example:

Cell Culture and Transfection Techniques

Primary neuronal cells were prepared as described in Example I. SP (SIGMA) at a concentration of 0.1 nM–100 $\mu$M was added 24–48 hrs after seeding, in the presence of 2.5% horse serum. When the cultures were maintained for more than 5 days, 10 $\mu$M cytosine arabinoside was added for 24 hours, beginning 3 days after plating the cells. Viability was quantified by trypan blue staining of the total cell population.

Human embryonic kidney 293T cells were grown as described in Example I. Transient transfection was performed using Superfect (Qiagen) as described by the manufacturer. Briefly, $2 \times 10^5$ cells/well were seeded into 35 mm wells 16 hr prior to transfection. Superfect:DNA complexes were added at a 5 $\mu$l:2 $\mu$g ratio for 3 hr; then the medium was replaced and after 24 hr SP was added. At 24–48 hr after addition of SP cell death was quantified as follows: the media containing floating cells were collected and centrifuged 10 min at 2000×g, the pellet was resuspended in PBS/trypan blue and the cells were counted using a hematocytometer. When other compounds were used, they were added at the same time as SP: zVAD.fmk or BAF was added at 50 $\mu$M and obtained from Enzyme System Products, Livermore, Calif.

Addition of Compounds to Cells:

The following compounds were added at the same time as SP in the indicated experiments: 5 nM L-732, 138; 1 nM L-733,060; 1 $\mu$g/ml Actinomycin D or 1 $\mu$g/ml Cycloheximide. All of these compounds were obtained from SIGMA. The caspase inhibitors zVAD.fmk and BAF were added at 50 $\mu$M and obtained from Enzyme System Products, Livermore, Calif.

NK1R Sub-cloning:

Briefly, the method entailed cloning the full-length (1.2 kb) NK1R cDNA (Genbank Accession No. M31477) by RT-PCR from adult rat hippocampal RNA into the XbaI/EcoRI sites of the vector pcDNA3.1 (Invitrogen), using the following oligonucleotides: forward 5'GGTCTATTGCCCCAAAATGGATAACG 3' (SEQ ID NO:2); reverse 5'CTGAATTCAAGATGGCTAGAGGCATGCC 3' (SEQ ID NO:3).

Nuclear Staining:

Either neuronal primary cultures or human embryonic kidney 293T cells were fixed with 4% paraformaldehyde and stained with 0.5 $\mu$g/ml DAPI (Molecular Probes) or Hoechst(SIGMA).

NK1R Immunostaining:

Cells were fixed 10 min with 4% paraformaldehyde; permeabilized 10 min with 2% Triton X-100/phosphate-buffered saline (PBS); washed with PBS, blocked 30 min with 4% goat serum/4% BSA/PBS; washed with PBS; incubated 16 hr at 4° C. with a 1:500 dilution of anti-NK1R (SIGMA); washed with PBS; incubated 30 min with 1:10,000 anti-rabbit antibody coupled to FITC or Texas Red (Molecular Probes) and washed with PBS.

Electron microscopy:

Human embryonic kidney 293T cells were grown to 50% confluency on poly-L-lysinecoated THERMANOX™ coverslips (13 mm, round, VWR-Scientific Products) and transfected with NK1R expression construct as described above. Pairs of duplicate coverslips were treated with 10 $\mu$M SP or vehicle alone for 24 hr, and then fixed with 2.0% paraformaldehyde/0.2% glutaraldehyde in 150 mM sodium cacodylate buffer, pH 7.4 (CB) at RT. Fixation was continued at 4° C. until the cells were washed well and postfixed in 2% osmium tetroxide (OsO4) (Electron Microscopy Sciences). They were reacted with 0.5% tannic acid (Sigma) followed by 1% NaSO4, and stained with 5% uranyl acetate in 50% ethanol during dehydration. Cells were flat embedded in Epon 812 between a second THERMANOX™ coverslip, and 3 or 4 samples from each sandwich were re-embedded in Epon blocks. En face thin sections were counterstained with uranyl acetate and lead citrate, and examined at 80 kV in a FEI-Philips Tecnai 12 (FEI-Philips, Hillsborough, Oreg.). Digital CCD images (Gatan Bioscan, Livermore, Calif.) were acquired in Digital Micrograph 1.0 (FEI-Philips) and trimmed in Adobe Photoshop 5.0.

Annexin-V Staining:

Cells were stained according to the manufacturer's instructions (Clontech). Briefly, cellswere washed with binding buffer and incubated with FITC-Annexin-V or EGF-PAnnexin-V for 5–10 min and fixed with 4% paraformaldehyde.

TUNEL Staining:

Cells were fixed 10 min with 4% paraformaldehyde and stained according to the manufacturer's instructions (Promega).

Protease Activation during SP-Induced Cell Death:

Preparation of cell-free extract for kinetic studies: 293T cells seeded at the density of 2 million cells per 10 cm dish were transfected with NK1R cDNA using Lipofectamine 2000 (Gibco) according the instructions provided by the manufacturer. After 24 hr 10 nM SP was added to half of the culture dishes. At 24 hr later the cells were washed with ice cold PBS and collected with a cell scraper. The cells pelleted at 700×g for 4 min were resuspended in cell lysis buffer at pH 7.4 containing 1 mM dithiothreitol at a ratio of 1:1 (v/v). After 30 min on ice the swelled cells were disrupted with 20 strokes using a 27 gauge needle and further spun at 16,000×g for 30 min. The pellet was discarded and the supernatant which represents the cytosolic fraction was aliquoted and stored at −80° C. or used in the kinetic studies. The protein concentration was determined using the Bradford assay (Pierce).

For kinetic studies, the proteolytic activities were followed fluorometrically by monitoring AFC or AMC release from 100 $\mu$M of the corresponding substrates (Enzyme Systems Products): Caspase-1 like, Ac-YVAD-AFC; caspase-2, Ac-VDVAD-AFC; caspases-3 like, Ac-DEVD-AFC; caspase-6, Ac-VEID-AFC; caspase-8, Ac-IETD-AFC; caspase-9, Ac-LEHD-AFC. Calpain activity was monitored with 100 $\mu$M Suc-LY-AFC (succinyl-Leu-Tyr-7-amino-4-methylcoumarin, Enzyme Systems Products) at 5 $\mu$M and 5 mM $CaCl_2$. The chymotrypsin activity of the proteasome was followed with 100 $\mu$M Suc-LLVY-AFC (succinyl-Leu-Leu-Val-Tyr-7-amino-4-methylcoumarin, Enzyme Systems Products), and cathepsins were assayed using 20 $\mu$M Z-FR-AMC (Benzyloxycarbonyl-Phe-Arg-7-amino-4-methylcoumarin, Bachem). A 10 $\mu$l aliquot of extract in the presence or absence of SP was added to 90 $\mu$l of substrate at the appropriate concentration and pH. The reaction was continuously monitored during 30 min and 37° C. in a fluorescence microplate reader (Molecular Devices). The instrument was set at excitation and emission wavelengths of 405 and 510 for AFC releasing group, and 370 and 460 nm, for AMC releasing group, respectively. The steady-state hydrolysis rates were obtained from the linear part of the curves.

EXAMPLE IV

The Role of the MAPK Pathway in SP-induced Paraptosis

This example demonstrates that the ERK-1/2 arm of the MAPK signaling pathway is involved in SP-induced paraptosis.

Figure 10A:
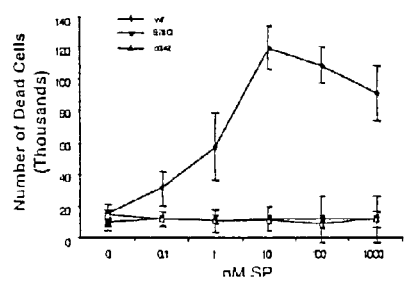
FIG. 10A shows the viability of cells transfected with NK1R constructs and treated with different concentrations of SP.

A carboxy-terminally truncated form of NK1R (NK1Rd342) has been reported to exhibit impaired endocytosis and SP-induced desensitization, with enhanced activation of a G-protein pathway increasing intracellular calcium levels (Bohm et al., *J Biol Chem* 272:2363–2372 (1997), Li, et al., *Proc Natl Acad Sci U S A*. 94:9475–9480 (1997)). The carboxy-terminal region of NK1R interacts with the scaffold protein β-arrestin, and upon SP stimulation, a protein complex is formed that activates the MAPK pathway leading to the activation of ERK-1 and ERK-2 (DeFea et al., supra). Since the MAPK pathway is impaired in the NK1Rd342 truncation, while the ability to activate G-proteins (the other major signaling pathway mediated by NK1R) remains intact, NK1Rd342 was tested for its capability of mediating SP-induced cell death. As shown in FIG. 10A, neither NK1Rd342 nor a NK1R point mutant that lacks SP binding (E78Q) (DeFea et al., supra 2000)) induced cell death in response to SP. The activation of ERK-1/2 by SP in 293T cells expressing the wild type NK1R, but not the NK1Rd342, was verified by Western blot using an antibody recognizing the phosphorylated form of ERK-1/2. In order to determine whether the MAPK pathway activated by SP is indeed required for NK1R-mediated non-apoptotic programmed cell death (pcd), the effect of the MEK inhibitor PD 98059 was evaluated. This kinase inhibitor is specific for the MEK that blocks the activation of ERK-1 and ERK-2. Non-neuronal NK1R-mediated pcd was inhibited by PD 98059, and PD 98059 effectively reduced the phosphorylation of ERK-1/2.

Figure 10B:
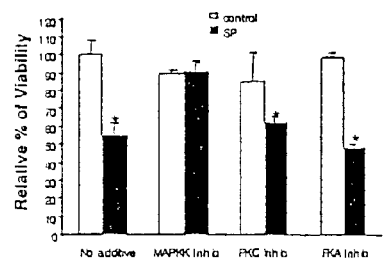
FIG. 10B shows the viability of striatal cells treated with protein kinase inhibitors in the presence or absence of SP.
Figure 10C:
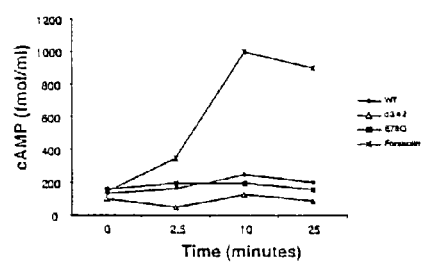
FIG. 10C shows the total intracellular cAMP produced in cells transfected with different plasmids and exposed to SP.
Figure 10D:
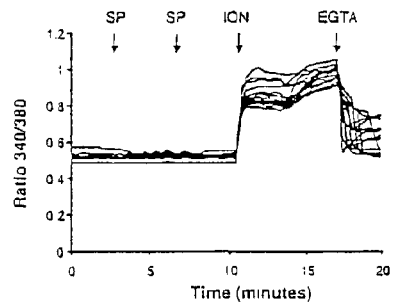
FIG. 10D shows the level of cytoplasmic calcium in striatal cells after the addition of SP, ionomycin and EGTA.

To rule out the participation of second messengers in the activation of this new death pathway, the production of cAMP in response to SP was quantified. Neither the wild type nor the mutant NK1Rd342 overexpressed in 293T cells generated a significant amount of cAMP, as compared with the production observed treating the cells with the adenylate cyclase activator forskolin (FIG. 10B). We then investigated whether the NK1R-mediated neuronal death was also dependent on a MEK that activated ERK-1/2. Neuronal cell death in response to SP was completely blocked by PD 98059 (MAPKK Inhib), whereas the addition of the PKC inhibitor Calphostin C or the PKA inhibitor Rp-8-Br-cAMPS had no protective effect (FIG. 10C). An increase in the amount of phosphorylated ERK-1/2 was observed after 10–30 min of SP stimulation, while the levels of total ERK-1/2 remained unchanged. A potential role for calcium signaling in this death pathway was rendered unlikely by the finding that SP did not induce a detectable change in cytoplasmic calcium in this system (FIG. 10D).

Activation of the MAPK pathway leads to the activation of ERK-1 and ERK-2. When the truncated form of NK1R is expressed in cells, these cells are resistant to SP-induced cell death while expression of wild-type NK1R results in SP-induced cell death. Furthermore, the MEK inhibitor compound PD 98059, which blocks the activation of ERK-1 and ERK-2, inhibits SP-induced cell death. Taken together, these results provide a ligand-receptor pair and associated signal transduction system by which to identify and modulate paraptotic processes.

In addition to the techniques described in the above examples, the following techniques were used in Example IV.

Addition of Compounds to Cells:

The protein kinase inhibitors were added 30 min before SP exposure at the following concentrations: 10 μM Rp-8-Br-cAMPS (adenosin 3',5'-cyclic monophosphorothioate, 8-bromo-, Rp-isomer, sodium salt) which is a PKA inhibitor; 50 nM Calphostin C, which is a PKC inhibitor; 10 μM PD 98059 which is a MAPKK (MEK) inhibitor. These compounds were obtained from Calbiochem. Viability was quantified by trypan blue staining of the total cell population.

NK1R Mutant Cloninq:

A NK1R construct was generated as described above in Example III. Briefly, the NK1R mutants were created using the QuickChange strategy (Stratagene, La Jolla, Calif., USA), using the following sequences for the oligonucleotides: 5'GTGGACCTGGCCTTCGCTCAGGCCTG-CATGGCTGCATTC 3' (SEQ ID NO:4) for NK1R E78Q mutation and 5'GGAAATGAAATCCACCCGATAC-CTCTAGGCATATTCAAGGCATGC 3' (SEQ ID NO:5) for NK1Rd342 truncation.

Western Blot Analysis to Detect ERK1/2 Phosphorylation:

For the transfected 293T cells, cells were washed with cold PBS after incubation with SP the time indicate and homogenized on lysis buffer (150 mM NaCl, 1% Triton X-100, 50 mM Tris HCL pH8.0). Cytoplasmic extracts were collected after 10 min centrifugation at 14,000 rcf. Total amount of protein was quantified by Bradford assay and electrophoresis of equal amounts of total protein was performed on SDS-polyacrylamide gels. Separated proteins were transferred to polyvinylidene fluoride membranes at 4° C. for Western blot analysis. Membranes were probed with a 1:1000 dilution of anti-ERK-1/2 or anti phospho-ERK-1/2 (BioSource). The blots were incubated in a horseradish peroxidase coupled secondary antibody for 1 h followed by enhanced chemiluminescence detection of the proteins with HYPERFILM™ ECL detection (Amersham, Arlington Heights, Ill.). For striatal neurons, total ERK-1/2 was immunoprecipitated using superparamagnetic Microbeads conjugated to protein A, following manufacture's instructions (MACS, Miltenyi Biotec), and then developed by Western blot against either anti-ERK-1/2 or anti phospho-ERK-1/2.

cAMP Quantification:

Total cellular cAMP was measured using the Biotrak-BIOTRAK™ non-acetylation enzymeimmunoassay system (Amersham Phramacia Biotech), following manufacturer's instructions. Forskolin (Sigma) was added at 10 μM.

Imaging of [Ca2+]c in Single Cells:

Single-cell imaging was performed in a Merlin imaging facility (Olympus America, USA) using an Olympus IX70 inverted epifluorescence microscope equipped with a 40× oil immersion objective and a Spectramaster monochromator (Life Science Resources, Cambridge, UK) (excitation, 340 and 380 nm; emission >505 nm). Cells were loaded with 3 µM Fura-2 AM (from TEF LABS, Texas, USA) for 30 min in incubation medium containing (in mM): 120 NaCl, 3.5 KCl, 1.3 CaCl2, 0.4 KH2PO4, 20 TES buffer, 5 NaHCO3, 1.2 Na2SO4, 15 Glucose, 1.2 MgCl2, pH adjusted to 7.4 with NaOH. 30 µg/ml bovine serum albumin was also added. Experiments were performed in a non-perfusing thermostatted chamber (37° C.) with incubation medium without bovine serum albumin (Castilho et al., *J. Neurosci.* 18:10277–10286 (1998)). 2 µM ionomycin (Sigma) and 10 mM EGTA (Sigma) were added at the times indicated in FIG. 5D.

All journal article, reference and patent citations provided above, including referenced sequence accession numbers of nucleotide and amino acid sequences contained in various databases, in parentheses or otherwise, whether previously stated or not, are incorporated herein by reference in their entirety.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

---

We claim:

1. A method of identifying a compound that modulates SP-induced paraptosis, comprising:
   (a) contacting a population of isolated cells expressing the neurokinin-1 receptor (NK1R) with an effective amount of substance P to induce SP-induced paraptosis;
   (b) contacting a first sub-population of said cells with a test-compound, and a second sub-population of cells with a control-compound; and
   comparing the amount of paraptotic cell death between said first and second sub-populations of cells indicates that said test-compound is a compound that modulates SP-induced paraptosis.

2. The method of claim 1, wherein said compound increases SP-induced paraptosis.

3. The method of claim 1, wherein said compound decreases SP-induced paraptosis.

4. The method of claim 1, wherein said cells are neuronal cells.

5. The method of claim 4, wherein said cells are selected from the group consisting of hippocampal, striatal and cortical cells.

6. The method of claim 1, wherein said test-compound is a nucleic acid.

7. The method of claim 1, wherein said test-compound is a small organic molecule.

8. The method of claim 1, wherein said test-compound modulates a MAPK pathway.

9. The method of claim 8, wherein said test-compound modulates the activity of a MAP kinase kinase that phosphorylates ERK1 or ERK2.

10. The method of claim 1, wherein said compound is AIP-1 or PD-98059.

* * * * *

UNITED STATES PATENT AND TRADEMARK OFFICE
CERTIFICATE OF CORRECTION

PATENT NO.        : 6,994,981 B2
APPLICATION NO.   : 10/202503
DATED             : February 7, 2006
INVENTOR(S)       : Sabina Sperandio et al.

It is certified that error appears in the above-identified patent and that said Letters Patent is hereby corrected as shown below:

1.    At column 43, claim 1, line 8, after "of" and before "cells", please insert therefore --said--.

2.    At column 43, claim 1, line 10, before "comparing", please insert therefore -- (c) --.

3.    At column 43, claim 1, line 11, after "cells" and before "indicates" please insert therefore --, wherein a difference in the amount of paraptotic cell death between said first and second sub-populations of cells--

Signed and Sealed this

Twenty-seventh Day of March, 2007

JON W. DUDAS
*Director of the United States Patent and Trademark Office*